United States Patent
Kurban et al.

(10) Patent No.: US 11,382,888 B2
(45) Date of Patent: Jul. 12, 2022

(54) COMBINATION OF TOPICAL MEDICATIONS FOR THE TREATMENT OF SKIN DISEASES AND METHODS OF USE

(71) Applicant: American University of Beirut, Beirut (LB)

(72) Inventors: Mazen Kurban, Beirut (LB); Nelly Rubeiz, Beirut (LB); Samar Khalil, Beirut (LB)

(73) Assignee: American University of Beirut, Beirut (LB)

( * ) Notice: Subject to any disclaimer, the term of this patent is extended or adjusted under 35 U.S.C. 154(b) by 2 days.

(21) Appl. No.: 16/863,104

(22) Filed: Apr. 30, 2020

(65) Prior Publication Data

US 2020/0345678 A1 Nov. 5, 2020

Related U.S. Application Data

(60) Provisional application No. 62/840,719, filed on Apr. 30, 2019.

(51) Int. Cl.
| | |
|---|---|
| *A61K 31/22* | (2006.01) |
| *A61P 17/00* | (2006.01) |
| *A61K 31/575* | (2006.01) |
| *A61K 31/47* | (2006.01) |
| *A61K 31/505* | (2006.01) |
| *A61K 31/496* | (2006.01) |
| *A61K 31/203* | (2006.01) |
| *A61K 31/405* | (2006.01) |
| *A61K 31/366* | (2006.01) |
| *A61K 45/06* | (2006.01) |

(52) U.S. Cl.
CPC ............ *A61K 31/22* (2013.01); *A61K 31/203* (2013.01); *A61K 31/366* (2013.01); *A61K 31/405* (2013.01); *A61K 31/47* (2013.01); *A61K 31/496* (2013.01); *A61K 31/505* (2013.01); *A61K 31/575* (2013.01); *A61P 17/00* (2018.01); *A61K 45/06* (2013.01)

(58) Field of Classification Search
CPC .... A61K 31/575; A61K 31/22; A61K 31/405; A61K 31/47; A61K 31/505; A61K 31/40; A61K 31/19; A61K 31/496; A61K 31/203; A61P 17/00
See application file for complete search history.

(56) References Cited

PUBLICATIONS

Bergqvist et al.; "CHILD syndrome: A modified pathogenesis-targeted therapeutic approach"; Epub: Feb. 2, 2018; Am. J. Med. Genet. A.; Mar. 2018; 176(3): 733-738; doi: 10.1002/ajmg.a.38619 (Year: 2018).*

Khalil et al.; "Use of Topical Glycolic Acid Plus a Lovastatin-Cholesterol Combination Cream for the Treatment of Autosomal Recessive Congenital Ichthyoses"; Sep. 12, 2018; JAMA Dermatol.; 154(11): 1320-1323; doi:10.1001/jamadermatol.2018.2904 (Year: 2018).*

Foldvari et al.; "Dermal drug delivery by liposome encapsulation: Clinical and electron microscopic studies"; Journal of Microencapsulation; 1990; 7(4); 479-489; doi: 10.3109/02652049009040470; PubMed abstract; PMID: 2266473 (Year: 1990).*

Alexopoulos A, et al. "CHILD Syndrome: Successful Treatment of Skin Lesions with Topical Simvastatin/Cholesterol Ointment—A Case Report." Pediatr Dermatol. 2015;32(4):e145-147.

Bergqvist C, et al. "CHILD syndrome: A modified pathogenesis-targeted therapeutic approach." Am J Med Genet A. 2018;176(3):733-738.

Bornholdt, D., et al. "Mutational spectrum of NSDHL in CHILD syndrome." Journal of Medical Genetics, 42(2), e17 (2005).

Christiansen AG, et al. "Skin Abnormalities in CHILD Syndrome Successfully Treated with Pathogenesis-based Therapy." Acta Derm Venereol. 2015;95(6):752-753.

Elias PM, et al. "Role of cholesterol sulfate in epidermal structure and function: lessons from X-linked ichthyosis." Biochim Biophys Acta. 2014;1841(3):353-361.

Fink-Puches,R., et al. "Systematized inflammatory epidermal nevus with symmetrical involvement: An unusual case of CHILD syndrome?" Journal of the American Academy of Dermatology, 36(5), 823-826. (1997).

Fink-Puches, R., et al. "Surgical treatment of CHILD nevus." European Journal of Dermatology, 10(4), 262-264 (2000). Abstract Only.

Hanyu O, et al. "Cholesterol sulfate induces expression of the skin barrier protein filaggrin in normal human epidermal keratinocytes through induction of RORα." Biochem Biophys Res Commun. 2012;428(1):99-104.

Happle, R., et al. "The CHILD syndrome." Congenital hemidysplasia with ichthyosiform erythroderma and limb defects. European Journal of Pediatrics, 134(1), 27-33 (1980).

Happle, R. "Ptychotropism as a cutaneous feature of the CHILDsyndrome." Journal of the American Academy of Dermatology, 23(4 Pt 1), 763-766 (1990).

Hernandez-Martin A, et al. "A systematic review of clinical trials of treatments for the congenital ichthyoses, excluding ichthyosis vulgaris." J Am Acad Dermatol. 2013;69(4):544-549 e548.

Ibsen HH, et al. "Topical cholesterol treatment of recessive X-linked ichthyosis." Lancet. 1984;2(8403):645.

Khalil S, et al. "Retinoids: a journey from the molecular structures and mechanisms of action to clinical uses in dermatology and adverse effects." J Dermatolog Treat 2017;28(8):684-696.

Khalil S, et al. "Use of Topical Glycolic Acid Plus a Lovastatin-Cholesterol Combination Cream for the Treatment of Autosomal Recessive Congenital Ichthyoses." JAMA dermatology. 2018; 154(11):1320-1323.

(Continued)

*Primary Examiner* — Timothy P Thomas
(74) *Attorney, Agent, or Firm* — J. Peter Paredes; Amin Talati Wasserman LLP

(57) ABSTRACT

The Combination of Topical Medications for the Treatment of Skin Diseases and Methods of Use is disclosed.

13 Claims, 19 Drawing Sheets

(19 of 19 Drawing Sheet(s) Filed in Color)

(56) References Cited

PUBLICATIONS

Kiritsi D, et al. "Targeting epidermal lipids for treatment of Mendelian disorders of cornification." Orphanet J Rare Dis. 2014;9:33.
Konig, A., et al. "Mutations in the NSDHL gene, encoding a 3beta-hydroxysteroid dehydrogenase, cause CHILD syndrome." American Journal of Medical Genetics, 90(4), 339-346 (2000).
König, A., et al. "A novel missense mutation of NSDHL in an unusual case of CHILD syndrome showing bilateral, almost symmetric involvement." Journal of the American Academy of Dermatology, 46(4), 594-596. (2002).
König, A., et al. "Donor dominance cures CHILD nevus." Dermatology, 220(4), 340-345 (2010).
Kraemer FB, et al. "Effects of ketoconazole on cholesterol synthesis." J Pharmacol Exp Ther. 1986;238(3):905-911.
Kurban, M., et al. "Late evolution of giant verruciform xanthoma in the setting of CHILD syndrome." Pediatric Dermatology, 27(5), 551-553 (2010).
Lykkesfeldt G, et al. "Topical cholesterol treatment of recessive X-linked ichthyosis." Lancet. 1983;2 (8363):1337-1338.
Oji V, et al. "Revised nomenclature and classification of inherited ichthyoses: results of the First Ichthyosis Consensus Conference in Soreze 2009." J Am Acad Dermatol. 2010;63(4):607-641.
Paller, A. S., et al. "Pathogenesis-based therapy reverses cutaneous abnormalities in an inherited disorder of distal cholesterol metabolism." Journal of Investigative Dermatolygy, 131(11), 2242-2248 (2011).
Rotstein, D. M. et al., "Stereoisomers of Ketoconazole: Preparation and Biology Activity" J. Med. Chem. (1992) 35, 2818-2825.
Seeger, M. A., et al. "The role of abnormalities in the distal pathway of cholesterol synthesis in the Congenital Hemidysplasia with Ichthyosiform erythroderma and Limb Defects (CHILD) syndrome." Biochimica et Biophysica Acta, 1841(3), 345-352 (2014).
Shimada M, et al. "Expression of a skin cholesterol sulfotransferase, St2b2, is a trigger of epidermal cell differentiation." Xenobiotica. 2008;38(12):1487-1499.
Strandberg TE, et al. "Effects of ketoconazole on cholesterol synthesis and precursor concentrations in the rat liver." Lipids. 1987;22(12):1020-1024.
Van Cutsem J, et al. "The antiinflammatory effects of ketoconazole. A comparative study with hydrocortisone acetate in a model using living and killed *Staphylococcus aureus* on the skin of guinea-pigs." J Am Acad Dermatol. 1991;25(2 Pt 1):257-261.
Van Wauwe JP, et al. "Ketoconazole inhibits the in vitro and in vivo metabolism of all-trans-retinoic acid." J Pharmacol Exp Ther 1988;245(2):718-722.
Xu, X. L., et al. Multiple verruciform xanthomas in the setting of congenital hemidysplasia with ichthyosiform erythroderma and limb defects syndrome. Pediatric Dermatology, 32(1), 135-137 (2015).

* cited by examiner

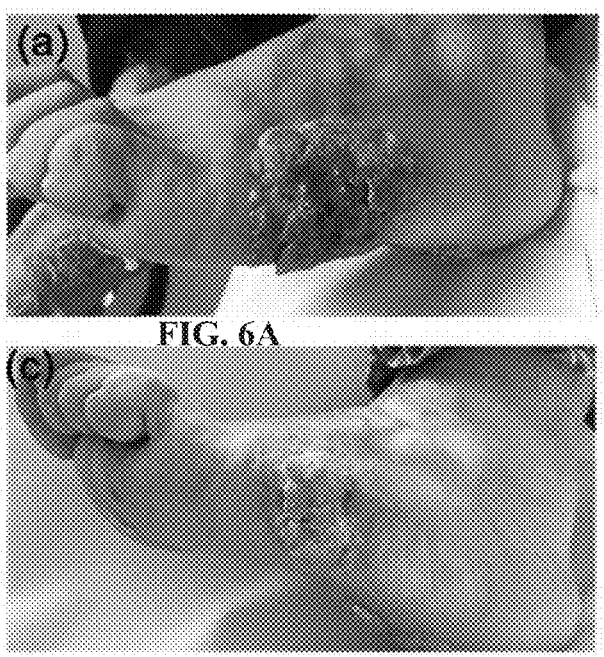
FIG. 6A
FIG. 6C
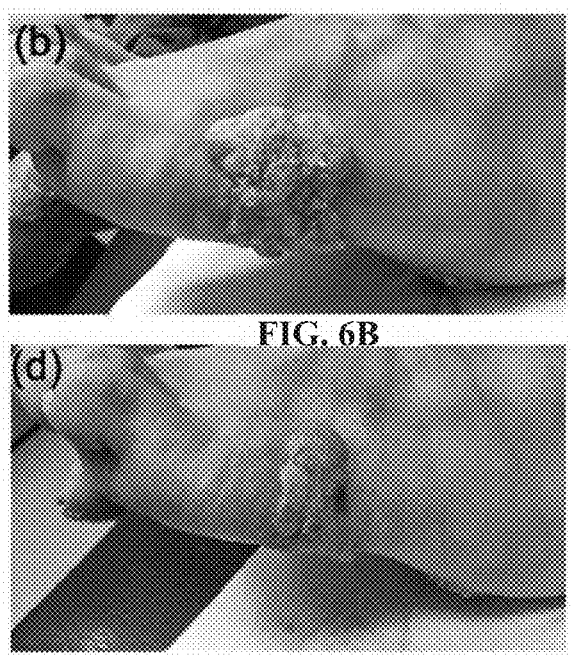
FIG. 6B
FIG. 6D

Table 1: Scores of the patients at baseline and on follow-up

| Patient ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | Average |
|---|---|---|---|---|---|---|---|---|---|---|---|---|---|---|---|---|---|---|---|---|---|---|---|---|---|
| At Baseline | | | | | | | | | | | | | | | | | | | | | | | | | |
| Skin thickness/ scaling | 16 | 14 | 17 | 10 | 15 | 20 | 16 | 17 | 15 | 7 | 15 | 7 | 9 | 15 | 7 | 7 | 0 | 20 | 10 | 18 | 12 | 18 | 13 | 16 | |
| Pain/ pruritis/ discomfort | 9 | 5 | 6 | 4 | 9 | 10 | 10 | 5 | 5 | 2 | 5 | 4 | 2 | 7 | 3 | 3 | 0 | 15 | 20 | 20 | 7 | 15 | 10 | 15 | |
| Erythema | 6 | 7 | 5 | 3 | 7 | 20 | 7 | 10 | 5 | 0 | 5 | 10 | 2 | 5 | 3 | 2 | 0 | 15 | 5 | 15 | 3 | 16 | 7 | 12 | |
| Impact of the condition on the ability to perform daily functions | 7 | 7 | 8 | 2 | 6 | 15 | 20 | 6 | 7 | 3 | 8 | 6 | 3 | 5 | 2 | 1 | 0 | 20 | 5 | 17 | 3 | 16 | 10 | 15 | |
| Patient severity scoring | 20 | 20 | 15 | 13 | 15 | 20 | 20 | 18 | 20 | 15 | 15 | 15 | 10 | 20 | 8 | 7 | 5 | 20 | 7 | 18 | 16 | 20 | 12 | 20 | |
| Total score | 58 | 53 | 51 | 32 | 52 | 85 | 73 | 56 | 52 | 27 | 48 | 42 | 26 | 52 | 23 | 20 | 5 | 90 | 47 | 88 | 41 | 85 | 52 | 78 | 51.5 |
| At 1 months | | | | | | | | | | | | | | | | | | | | | | | | | |
| Skin thickness/ scaling | 4 | 3 | 7 | 1 | 4 | 15 | 6 | 14 | 15 | 9 | 10 | 5 | 2 | 5 | | | | 15 | 7 | 15 | 7 | 14 | 5 | | |
| Pain/ pruritis/ discomfort | 2 | 1 | 4 | 1 | 1 | 8 | 4 | 5 | 5 | 2 | 0 | 2 | 1 | 2 | | | | 10 | 10 | 16 | 5 | 12 | 5 | | |
| Erythema | 2 | 1 | 4 | 1 | 5 | 15 | 3 | 7 | 5 | 0 | 0 | 5 | 1 | 2 | | | | 12 | 4 | 10 | 3 | 14 | 0 | | |
| Impact of the condition on the ability to perform daily functions | 2 | 1 | 3 | 0 | 3 | 10 | 3 | 4 | 5 | 3 | 0 | 4 | 0 | 2 | | | | 10 | 4 | 14 | 3 | 12 | 0 | | |
| Patient severity scoring | 7 | 5 | 7 | 5 | 9 | 13 | 6 | 18 | 18 | 10 | 10 | 10 | 1 | 7 | | | | 10 | 5 | 15 | 12 | 15 | 5 | | |
| Total score | 17 | 11 | 25 | 8 | 22 | 61 | 22 | 48 | 48 | 24 | 20 | 26 | 5 | 18 | 3 | 2 | | 57 | 30 | 70 | 30 | 67 | 15 | | 31.2 |
| % change | 70 | 79 | 51 | 75 | 57 | 28 | 69 | 14 | 7 | 11 | 58 | 38 | 80 | 73 | | | | 36 | 36 | 20 | 26 | 21 | 71 | | 46.4 |
| | .7 | .2 | | .0 | .7 | .2 | .9 | .3 | .7 | .1 | .3 | .1 | .8 | .1 | | | | .7 | .2 | .8 | .8 | .2 | .1 | | |
| Response | V G | V E G | E G | E G | V E G | G | V G | F | P | F | V F G | G | E E | V E G | | | | G | G | F | G | F | V G | | G |
| At 2 months | | | | | | | | | | | | | | | | | | | | | | | | | |
| Skin thickness/ scaling | 10 | 2 | | | 2 | 20 | 4 | 15 | 10 | 10 | 5 | | | | 3 | 2 | | 12 | 5 | 12 | 5 | 16 | | | |

FIG. 8

| | | | | | | | | | | | | | | |
|---|---|---|---|---|---|---|---|---|---|---|---|---|---|---|
| Pain/ pruritis/ discomfort | 6 | 1 | 1 | 10 | 2 | 5 | 0 | 0 | 0 | 10 | 0 | 0 | 8 | 5 | 10 | 2 | 13 | | |
| Erythema | 4 | 3 | 8 | 20 | 2 | 0 | 0 | 0 | 0 | 3 | 1 | 0 | 10 | 0 | 0 | 2 | 16 | | |
| Impact of the condition on the ability to perform daily functions | 3 | 0 | 1 | 15 | 3 | 0 | 0 | 0 | 0 | 6 | 0 | 0 | 8 | 2 | 1 | 0 | 14 | | |
| Patient severity scoring | 13 | 3 | 3 | 20 | 4 | 18 | 16 | 10 | 10 | 8 | 3 | 3 | 8 | 5 | 13 | 9 | 17 | | |
| Total score | 36 | 9 | 15 | 85 | 15 | 38 | 31 | 20 | 20 | 32 | 7 | 3 | 46 | 17 | 36 | 18 | 76 | | |
| % change | 37 83 9 0 | | 71 10 | | 79 4 | 32 1 | 40 4 | 25 9 | 58 3 | 23 8 | 89 6 | 75 40 9 | 46 9 | 63 8 | 69 1 | 56 1 | 10 8 | | |
| Response | G | E | E | P | E | G | G | G | G | G > V F | VG > V G | E G | G G | G G | V > G G | V > G F | | | |
| At 3 months | | | | | | | | | | | | | | | | | | | |
| Skin thickness/ scaling | 7 | 1 | 2 | | 4 | 8 | 12 | 6 | | | | | 7 | 4 | | | 5 | | |
| Pain/ pruritis/ discomfort | 5 | 0 | 1 | | 2 | 1 | 0 | 0 | | | | | 6 | 5 | | | 4 | | |
| Erythema | 3 | 3 | 7 | | 2 | 2 | 0 | 0 | | | | | 7 | 0 | | | 10 | | |
| Impact of the condition on the ability to perform daily functions | 2 | 0 | 1 | | 3 | 3 | 0 | 0 | | | | | 6 | 2 | | | 5 | | |
| Patient severity scoring | 8 | 1 | 2 | | 3 | 14 | 13 | 9 | | | | | 6 | 5 | | | 9 | | |
| Total score | 25 | 5 | 13 | | 14 | 28 | 25 | 15 | | | | | 32 | 16 | | | 33 | 20.6 | |
| % change | 56 80 9 0 | | 75 | | 80 9 | 50 9 | 51 9 | 44 4 | | | | | 84 4 | 68 | | | 57 7 | 63.8 | |
| Response | V > G G | E | E | | E | V > G G | V > G G | G | | | | | V > G G | V > G G | | | V > G G | VG | |
| At 4 months | | | | | | | | | | | | | | | | | | | |
| Skin thickness/ scaling | 11 | 1 | 1 | | 7 | 12 | 8 | 3 | | | | | | 3 | | | | | |
| Pain/ pruritis/ discomfort | 6 | 1 | 1 | | 4 | 10 | 0 | 1 | | | | | | 5 | | | | | |

FIG. 8 (cont.)

|  | 4 | 2 | 1 | 4 | 4 | 0 | 2 |  | 0 |  |  |
|---|---|---|---|---|---|---|---|---|---|---|---|
| Erythema | 4 | 2 | 1 | 4 | 4 | 0 | 2 |  | 0 |  |  |
| Impact of the condition on the ability to perform daily functions | 5 | 0 | 0 | 4 | 0 | 0 | 2 |  | 0 |  |  |
| Patient severity scoring | 15 | 0 | 3 | 6 | 15 | 11 | 8 |  | 5 |  |  |
| Total score | 41 | 4 | 8 | 25 | 41 | 19 | 16 |  | 13 |  | 20.6 |
| % change | 29 | 92 | 81 | 68 | 21 | 29 | 61 |  | 72 |  | 56.7 |
|  | 3 | 4 | 2 | 7 | 1 | 6 | 9 |  | 3 |  |  |
| Response | G | E | E | VG | F | G | VG |  | VG |  | VG |
| At 5 months |  |  |  |  |  |  |  |  |  |  |  |
| Skin thickness/ scaling |  | 3 | 1 |  |  |  |  | 7 | 4 | 1 |  |
| Pain/ pruritis/ discomfort |  | 1 | 1 |  |  |  |  | 7 | 10 | 1 |  |
| Erythema |  | 3 | 5 |  |  |  |  | 0 | 0 | 0 |  |
| Impact of the condition on the ability to perform daily functions |  | 0 | 1 |  |  |  |  | 0 | 0 | 0 |  |
| Patient severity scoring |  | 2 | 1 |  |  |  |  | 7 | 4 | 2 |  |
| Total score |  | 9 | 9 |  |  |  |  | 21 | 18 | 4 | 12.2 |
| % change |  | 83 | 82 |  |  |  |  | 87 | 10 | 20 | 40.9 |
|  |  | 0 | 7 |  |  |  |  |  |  |  |  |
| Response |  | E | E |  |  |  |  | P | F | F | G |
| At 6 months |  |  |  |  |  |  |  |  |  |  |  |
| Skin thickness/ scaling | 10 |  |  |  |  |  |  |  |  |  |  |
| Pain/ pruritis/ discomfort | 5 |  |  |  |  |  |  |  |  |  |  |
| Erythema | 0 |  |  |  |  |  |  |  |  |  |  |

FIG. 8 (cont.)

| | |
|---|---|
| Impact of the condition on the ability to perform daily functions | 0 |
| Patient severity scoring | 10 |
| Total score | 25 |
| % change | 51 |
| Response | VG |

*P: Poor; F: Fair; G: Good; VG: Very good; E: Excellent*

FIG. 8 (cont.)

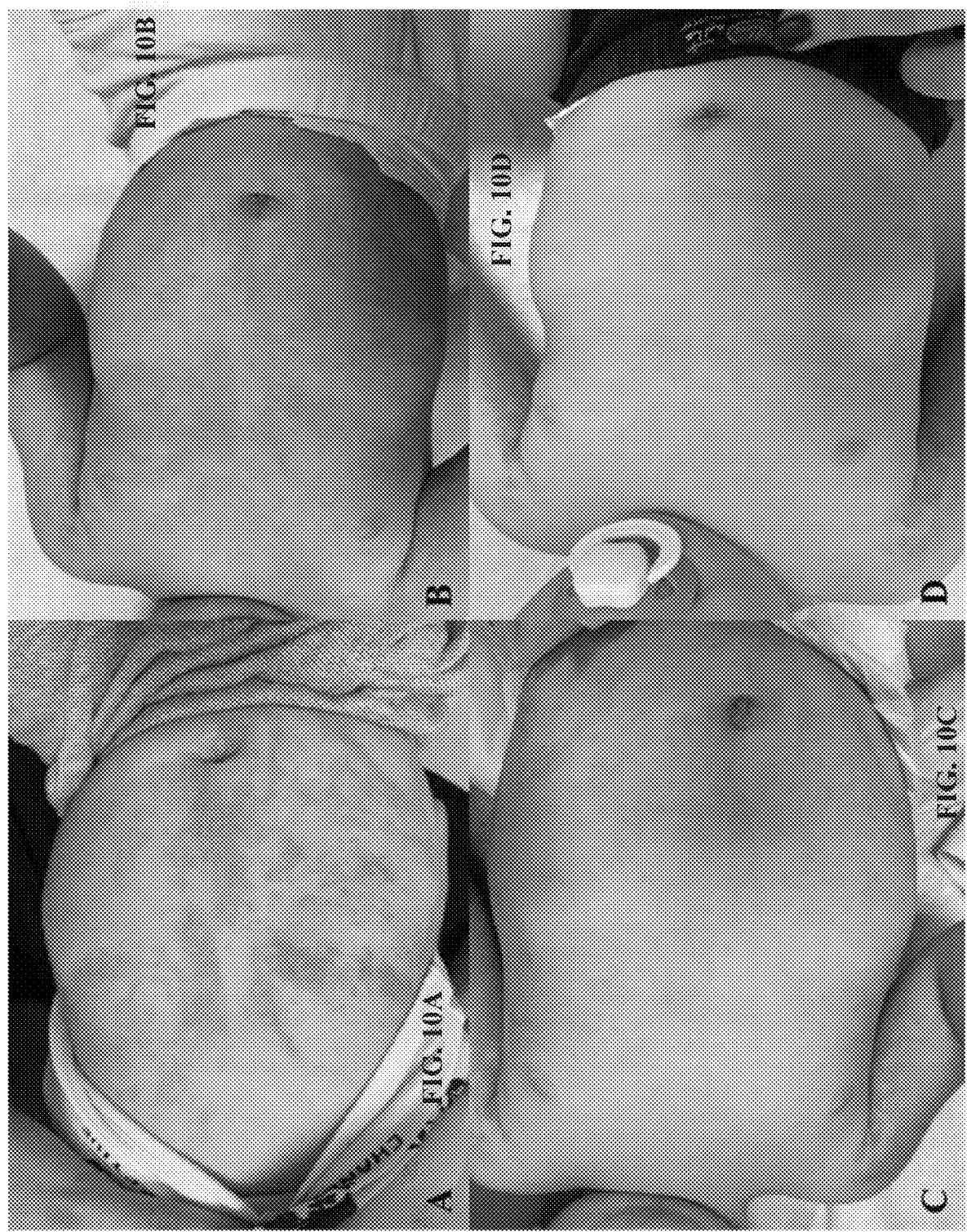

COMBINATION OF TOPICAL MEDICATIONS FOR THE TREATMENT OF SKIN DISEASES AND METHODS OF USE

CROSS-REFERENCE TO RELATED APPLICATIONS

The present application claims priority to U.S. provisional application Ser. No. 62/840,719, filed Apr. 30, 2019, herein incorporated by reference in its entirety.

BACKGROUND

The invention generally relates to pharmaceutical compositions containing compounds and also to the use of these compounds and of these compositions for the treatment of pathological conditions.

Ichthyosis refers to a set of inherited and acquired disorders of keratinization in which the skin is covered by an excessive amount of scales, resulting in a thick yet dysfunctional skin barrier. Among the most commonly encountered inherited nonsyndromic ichthyoses in Lebanon is a subgroup referred to as Autosomal Recessive Congenital Ichthyosis (ARCI).[1] The mainstay of treatment involves the use of hydrating agents and keratolytics, including topical glycolic acid, urea, salicylic acid, and retinoids, among others. Systemic retinoids can also be used in select cases.[2]

The formation of the physiologic skin barrier and its normal differentiation rely on the normal production of lipids, particularly cholesterol. Disturbances in cholesterol production and metabolism are involved in the pathogenesis of many skin diseases, including ichthyosis.[3]

Topical cholesterol replacement has been previously used, with variable success, in the management of x-linked ichthyosis caused by mutations in the steroid sulfatase gene.[4,5] Our research group and others' have used a combination of lovastatin, 2%, and cholesterol, 2%, cream for the treatment of cutaneous manifestations in a rare ichthyosiform condition known as CHILD syndrome (congenital hemidysplasia ichthyosis and limb defects). The lovastatin serves to inhibit local 3-hydroxy-3-methyl-glutaryl-coenzyme A reductase enzyme activity and thus the production of toxic metabolites, and the cholesterol compensates for the endogenous cholesterol normally produced in the skin.[6-9]

SUMMARY OF THE INVENTION

Provided herein are systems, methods and compositions for a combination topical therapy for the treatment of resistant cases of ARCI, ichthyosiform, and CHILD syndrome.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In the accompanying figures, like elements are identified by like reference numerals among the several preferred embodiments of the present invention.

FIG. 3A is a photograph showing the linear brown verrucous plaques arranged along the lines of Blaschko, more pronounced on the right side of body. FIG. 3B is a photograph showing the face covered by brown linear plaques with associated thinning of hair. FIG. 3C is a photograph of a tongue covered by confluent fleshy verrucous papules. FIGS. 3D-3E are photographs of the right palm and dorsum of right hand showing thick yellowish linear plaques, respectively.

FIG. 4A is a photograph of a verruciform xanthoma at presentation. FIG. 4B is a photograph after 6 weeks of treatment. [Color figure can be viewed at wileyonlinelibrary.com]

FIG. 5A is a photograph of verruciform xanthoma at presentation. FIG. 5B is a photograph after 4 weeks of treatment. FIG. 5C is a photograph after 8 weeks of treatment. FIG. 5D is a photograph after 14 weeks of treatment. FIG. 5E is a photograph after 20 weeks of treatment. FIG. 5F is a photograph after 28 weeks of treatment.

FIGS. 6A-6D are photographs of Case 2: The effect of 2% cholesterol and 2% lovastatin cream on verruciform xanthoma of the left foot. FIG. 6A is a photograph of verruciform xanthoma at presentation FIG. 6B is a photograph after 6 weeks of treatment. FIG. 6C is a photograph after 20 weeks of treatment. FIG. 6D is a photograph after 42 weeks of treatment.

FIG. 8 is a table showing the scores of the patients at baseline and on follow-up.

FIG. 9A is a photograph of a patient ID-11 before treatment; FIG. 9B is a photograph of patient ID-11 after 1 month of treatment; FIG. 9C is a photograph of patient ID-11 after 2 months of treatment; and FIG. 9D is a photograph of patient ID-1 after 4 months of treatment.

FIG. 10A is a photograph of a patient ID-13 before treatment; FIG. 10B is a photograph of patient ID-13 after 1 month of treatment; FIG. 10C is a photograph of patient ID-13 after 2 months of treatment; and FIG. 10D is a photograph of patient ID-13 after 4 months of treatment.

DETAILED DESCRIPTION OF THE INVENTION

Figure 1A:
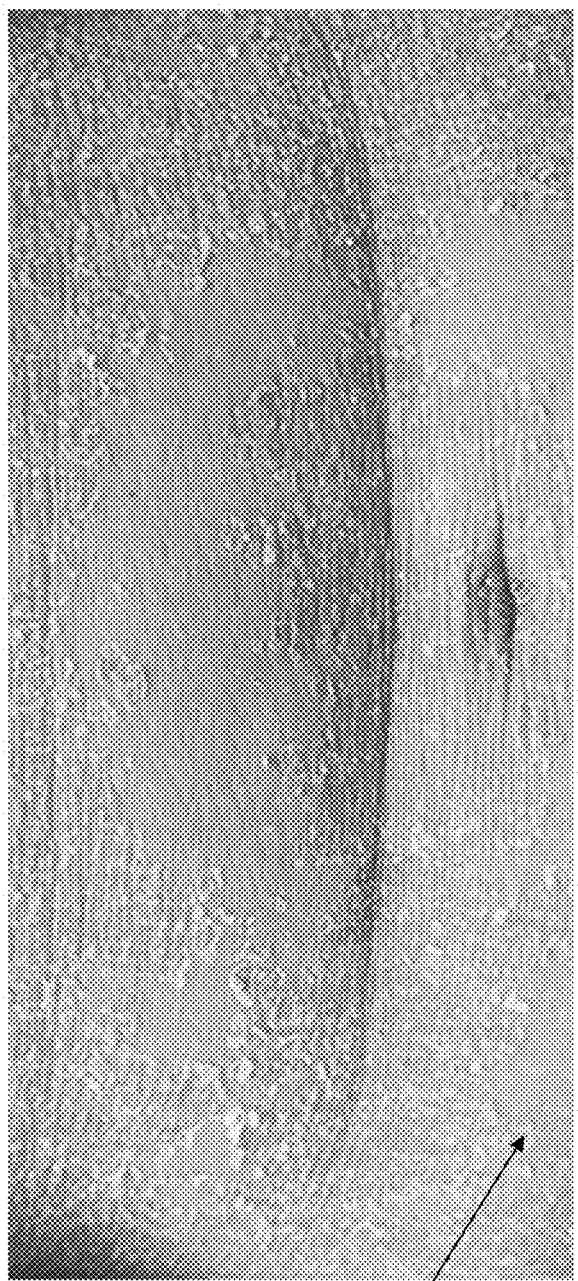
FIGS. 1A-1B are photographs of a Patient 4 before (FIG. 1A) and 3 months after (FIG. 1B) treatment with the study medication. A very good response was noted, i.e., 72.7% improvement from baseline in the disease severity score.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Inherited ichthyosiform and ichthyosiform disorders are rare disorders with no convincing treatment currently exist. To date, the best treatment consists of oral retinoic acid, yet this is not without toxicity/side effects. Topical treatment includes hydrating creams, urea, salicylic acid, glycolic acid and propylene glycol. The current topical formulations are of limited efficacy and the majority of patients are not satisfied. According to the preliminary data, marked improvement in several patients with ichthyosiform and ichthyosiform disorders by the present invention.

In one embodiment, a combination of cholesterol at about 2% by weight and lovastatin at about 2% by weight in a cream base and another cream of either glycolic acid at about 10% by weight or at about 20% by weight. In one embodiment, the glycolic acid cream at about 10% by weight is to be applied over the face and the glycolic acid cream at about 20% by weight is applied over the body. This formulation is Formulation 1. Cholesterol may be between about 2% by weight to about 15% by weight may be used in Formulation 1. Lovastatin may be between about 2% by weight to about 15% by weight may be used in Formulation 1. Glycolic acid cream may be between 10% by weight to about 70% by weight in Formulation 1.

As used herein, "lovastatin" includes its analogs or derivatives", which refer to a class of compounds including pharmaceutically acceptable analogs, derivatives, esters, prodrugs, salts, solvates, enatiomers, stereoisomers, active metabolites, co-crystals, and other physiologically functional derivatives of lovastatin. Such lovastatin analogs or derivatives may be used as lipid lowering agents. However, the prior use of the lovastatin analogs or derivatives does not necessarily imply a mechanism of action in the treatment of methanogenesis. That is, in some embodiments, the lovastatin analog or derivative may inhibit the enzyme HMG-CoA reductase while in others it may have another manner of causing an effect. For example, the lovastatin analog or derivative may target a methanogenic enzyme, such as, for example, one or more of adh alcohol dehydrogenase; fdh formate dehydrogenase; fno F420-dependent NADP oxidoreductase; ftr formyl-MF:H4MPT formyltransferase; fwd formyl-MF dehydrogenase; hmd methylene-H4MPT dehydrogenase; mch methenyl-H4MPT cyclohydrolase; mtd F420-dependent methylene-H4MPT dehydrogenase; mer F420-dependent methylene-H4MPT reductase; mtr methyl-H4MPT:CoM-methyltransferase; mcr methyl-CoM reductase; and the mtaB methanol:cobalamin methyltransferase heterodisulfide reductase system. In some embodiments, the lovastatin analog or derivative does not substantially inhibit the enzyme HMG-CoA reductase. In some embodiments, the lovastatin analog or derivative is present in the lactone form, for example, as the active form (e.g. in a subject's GI tract). In some embodiments, the lovastatin analog or derivative is lovastatin diol lactone.

The present invention contemplates the use of lovastatin analogs or derivatives and other statins, which includes pharmaceutically acceptable analogs, esters, prodrugs, salts, solvates, enatiomers, stereoisomers, active metabolites, co-crystals, and other physiologically functional derivatives of lovastatin. Lovastatin, also known as mevinolin, was described, for example, in U.S. Pat. No. 4,231,938, the entire contents of which are incorporated by reference herein. Various anti-methanogenic lovastatin analogs or derivatives thereof are contemplated. In various embodiments, any of these anti-methanogenic lovastatin analogs or derivatives are in the lactone form (e.g. substantially in the lactone for, or in an equilibrium in which the lactone form is predominant of the beta-hydroxy form), where applicable. 3-hydroxy-3-methyl glutaryl coenzyme A (HMG-CoA) reductase inhibitors (known as HMG-CoA inhibitors, or "statins"). Statins inhibit the enzyme HMG-CoA reductase, which controls the rate of cholesterol production in the body. The HMG CoA inhibitor is selected from the group consisting of pitavastatin, atorvastatin, rosuvastatin, fluvastatin, lovastatin, pravastatin and simvastatin.

Figure 7:
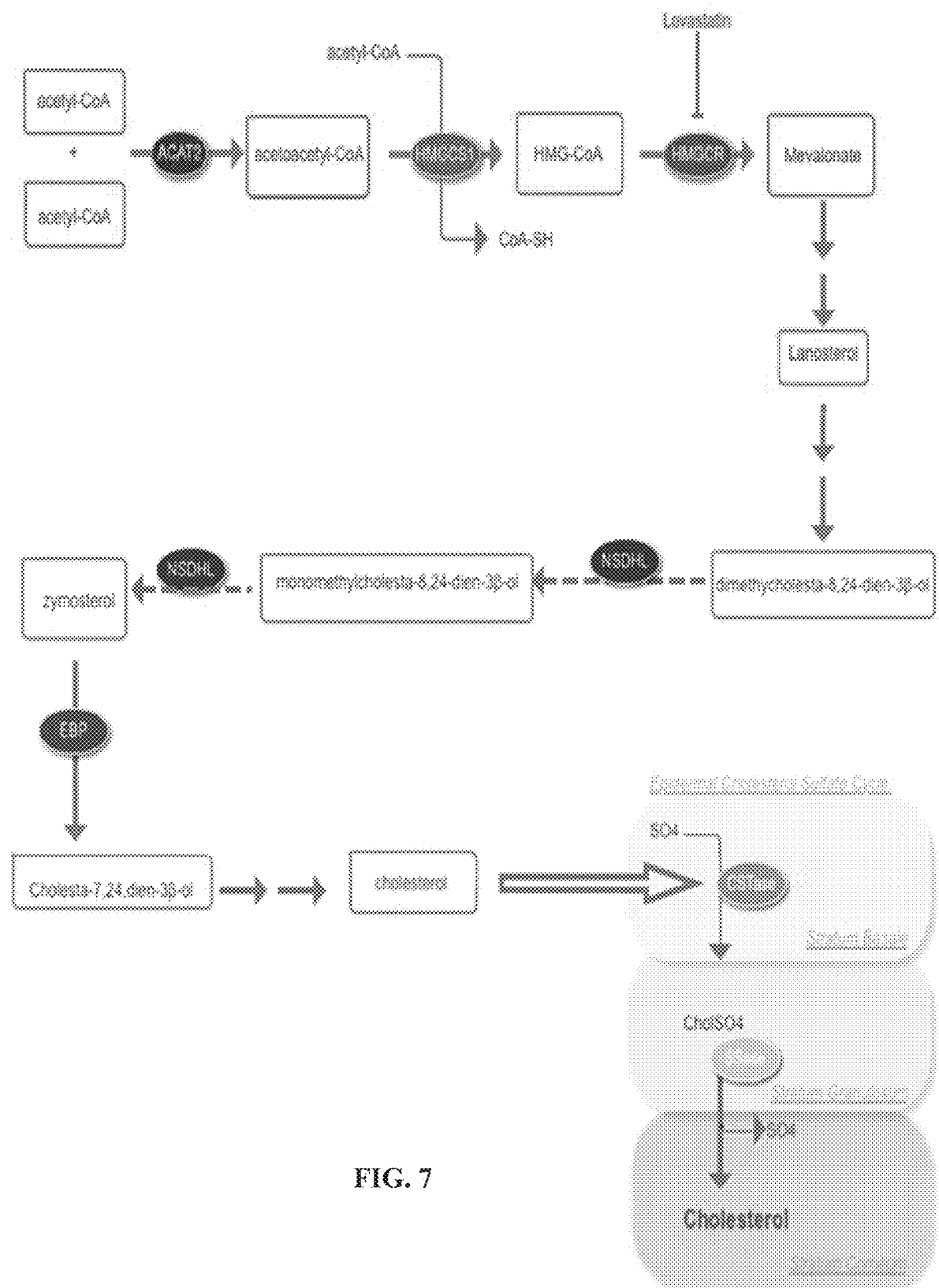
FIG. 7 is a schematic of the cholesterol metabolic pathway and the cholesterol sulfate cycle.
Figures 11A, 11B, 11C:
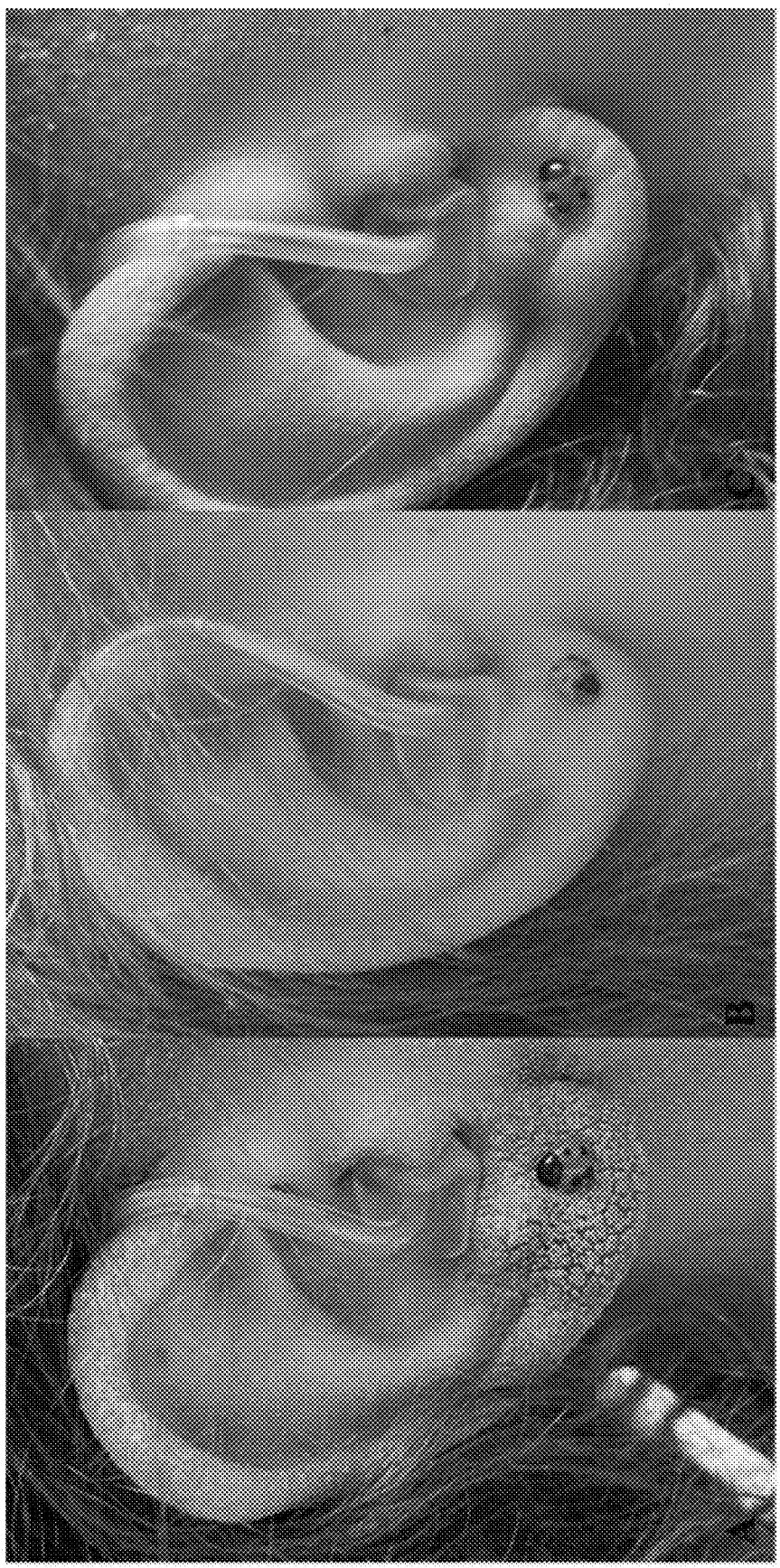
FIG. 11A is a photograph of a patient ID-15 before treatment.
FIG. 11B is a photograph of patient ID-15 after 1 month of treatment.
FIG. 11C is a photograph of patient ID-15 after 2 months of treatment.
Figures 12A, 12B:
FIG. 12A is a photograph of a patient ID-15 before treatment.
FIG. 12B is a photograph of patient ID-15 after 1 month of treatment.
Figures 13A, 13B:
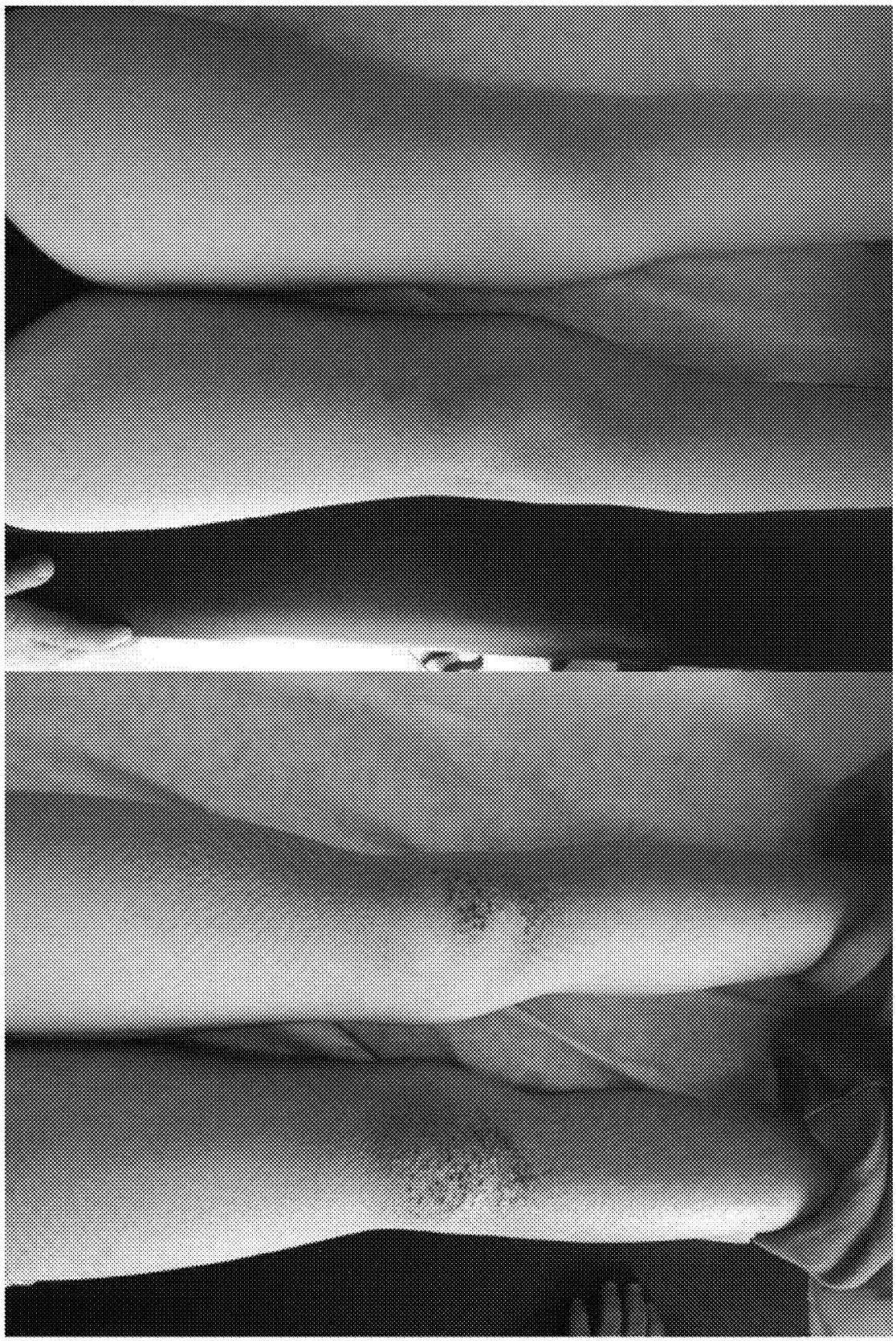
FIG. 13A is a photograph of Patient ID-14, before treatment.
FIG. 13B is a photograph of patient ID-14 after 1 month of treatment, showing a very good response.
Figure 14:
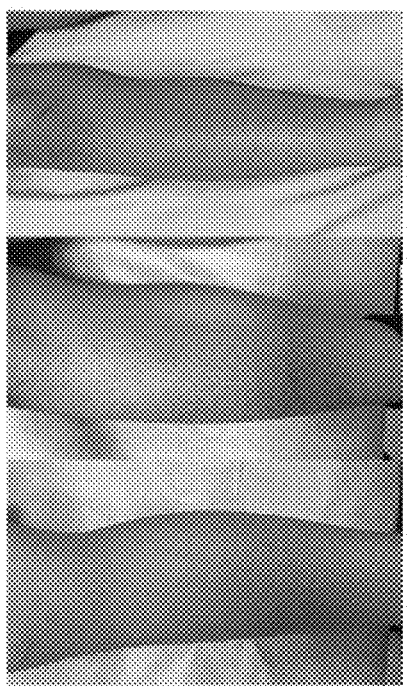
FIG. 14A is a photograph of Patient ID-23 before treatment.
FIG. 14B is a photograph of patient ID-23 after 2 weeks of treatment.
FIG. 14C is a photograph of patient ID-23 after 1 month treatment, showing a very good response.
Figure 15:
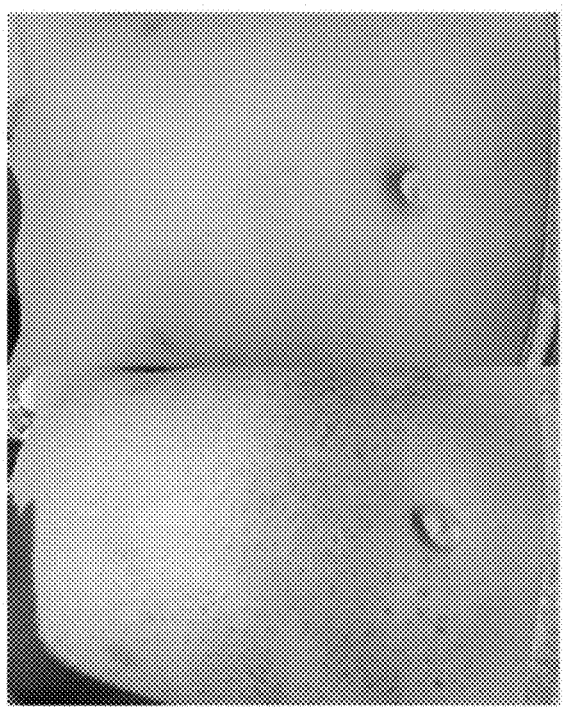
FIG. 15A is a photograph of Patient ID-23 before treatment.
FIG. 15B is a photograph of patient ID-23 after 1 month of treatment, showing an excellent response.
Figure 16:
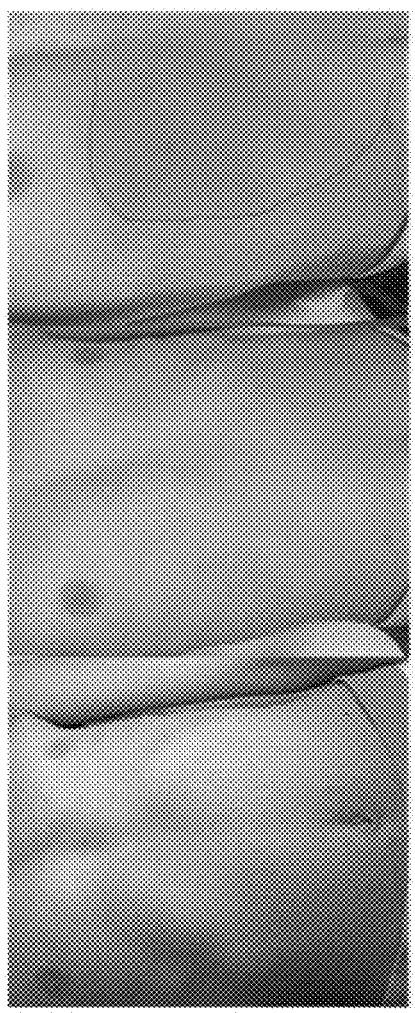
FIG. 16A is a photograph of Patient ID-4 before treatment.
FIGS. 16B-16C are photographs of patient ID-4 after 4 months of treatment, showing an excellent response, where a clear demarcation line is drawn between the treated and untreated areas on the abdomen in FIG. 16C.
Figure 17:
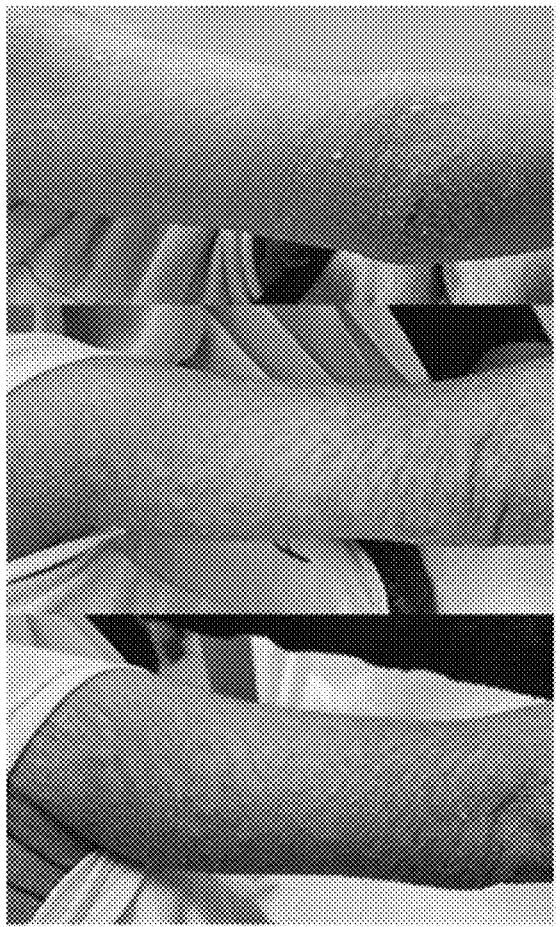
FIG. 17A is a photograph of Patient ID-3 before treatment.
FIG. 17B is a photograph of patient ID-3 after 1 month of treatment, showing a very good response.
Figure 19:
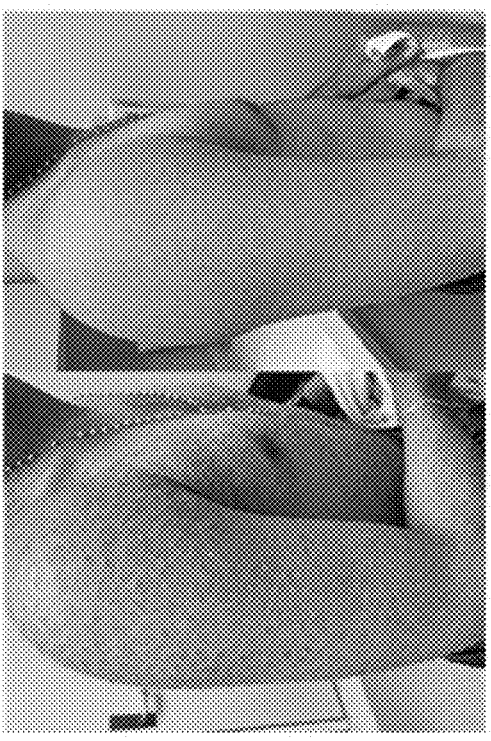
FIG. 19A is a photograph of Patient ID-8 before treatment.
FIG. 19B is a photograph of patient ID-8 after 1 month of treatment with a fair response.
FIG. 19C is a photograph of patient ID-8 after 3 months of treatment showing a very good response.
Figure 18:
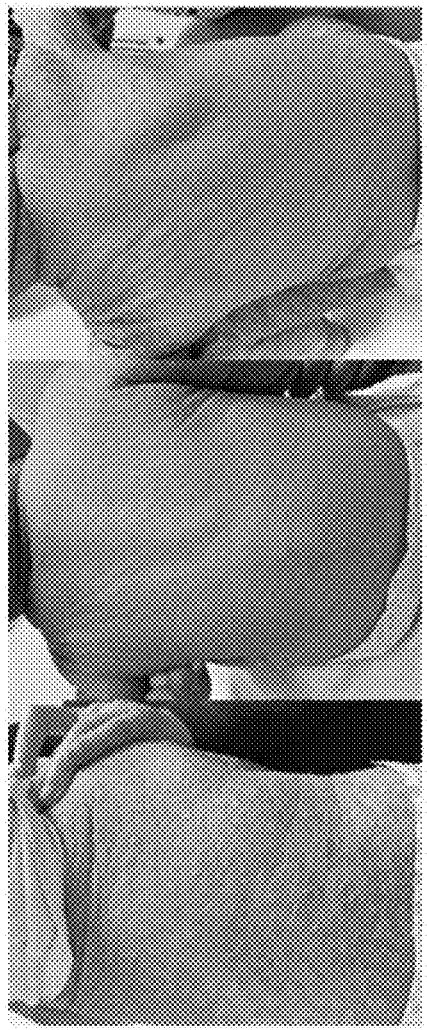
FIG. 18A is a photograph of Patient ID-1 before treatment.
FIG. 18B is a photograph of patient ID-1 after 1 month of treatment.
FIG. 18C after 3 months of treatment, showing a very good response, where at the 3 months follow-up visit, the patient had been suffering from fever and an upper respiratory tract infection which likely contributed to worsening of his condition.

The cholesterol metabolic pathway and the cholesterol sulfate cycle are shown in FIG. 7. Synthesis of cholesterol starts with the condensation of two molecules of acetyl-CoA. The rate limiting step is catalyzed by HMG-CoA reductase, the enzyme targeted by statins. After being formed, cholesterol is sulfated by the enzyme cholesterol sulfotransferase (SULT2B1b) in the lower epidermis to form cholesterol sulfate. The latter is then de-sulfated by the enzyme steroid sulfatase (SSase) in the outer epidermis.

In accordance with a preferred embodiment of the invention, Lovastatin is the inhibitor of cholesterol synthesis which inhibits the HMG-CoA reductase, and may be substituted with other inhibitors of HMG-CoA reductase such as Fluvastatin, Pravastatin Simvastatin, Atervastatin, Cerivastatin and Crilvastatin.

Glycolic acid of formula $CH_2(OH)COOH$, also known as hydroxyacetic acid. In certain embodiments, the compositions of the present invention can include from about 0.001% to about 20%, by weight or volume, of glycolic acid compounds, or a combination of both. It should be recognized, however, that the amount of the compounds in a composition can be modified below, within, or above this range based on the desired results (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 96, 97, 98, 99%, or more, by weight or volume of the composition). Therefore, the amount of a glyceryl/acid or glycol/acid compound can include less than 0.001% or more than 5%, by weight or volume. In other aspects, the compositions can include 0.002, 0.003, 0.004 . . . 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more or, or any range derivable therein, by weight or volume of glyceryl or glycol salicylate or a combination of both.

Cholesterol exists in substantially all plant and animal cells either in the free form or as an ester. It often exists in admixture with one or more of its derivatives such as dehydrocholesterol, 7-dehydrocholesterol, etc. Cholesterol derivatives include dehydrocholesterol, 7-dehydrocholesterol, cholesterol esters, etc.

In another embodiment, a second preparation, this is also constituted of two combinations. The first combination consists of cholesterol at about 2% by weight and lovastatin at about 2% by weight in a cream base and the second combination is made of glycolic acid at about 10% by weight, 2% ketoconazole at about 2% by weight, and retinoic acid at about 0.025% by weight. This formulation is Formulation 2. Alternatively, ketoconazole may substituted with another antifungal drug, as indicated below. Ketoconazole may be between about 0.1% and 10% by weight in formulation 2. Cholesterol may be between about 2% by weight to about 15% by weight may be used in Formulation 1. Lovastatin may be between about 2% by weight to about 15% by weight may be used in Formulation 1. Glycolic acid cream may be between 10% by weight to about 70% by weight in Formulation 1. Retinoic acid between about 0.025% by weight and 0.1% by weight.

In another embodiment, a third preparation consists of glycolic acid, statin, and cholesterol. Glycolic acid is about 10% by weight, and is applied on the face; and glycolic acid at about 15% by weight or about 20% by weight, is applied on the body. The frequency of application varied from nightly application to every other night, depending on tolerability. The combination cream of lovastatin at about 2% by weight, and cholesterol at about 2% by weight.

Several dermatological conditions including ichthyosis could benefit from applying retinoids on the skin. Experiments showed that (RA)—treated skin result in hyperproliferation of basal keratinocytes and thickening of the epidermis, followed by clinical peeling and desquamation. At the molecular level, (RA) binds nuclear steroidogenic receptors which regulate the expression of genes for cell growth control and ligands for epidermal growth factor (EGF).

In one embodiment, the method comprises using the 0.025% of retinoic acid by weight to treat an appropriate skin differentiation. Ketoconazole is an antifungal drug that has been used for that purpose for many years. Interestingly, ketoconazole is an inhibitor of CYP26A1. CYP26A1 encodes for an enzyme that degrades retinoic acid. Thus inhibition of retinoic acid degradation in the skin with concomitant use of retinoic acid 0.025% by weight carries the potential to improve the skin conditions. As for the 10% glycolic acid by weight, it will help in desquamating superficial part of the epidermis allowing the better penetration of the combinatorial medications used.

Ketoconazole, 1-acetyl-4-[4-[[2-(2,4-dichlorophenyl)-2-[(1H-imidazol-1-yl)-methyl]-1,3 -dioxolan-4-yl]methoxy]

phenyl]piperazine, is a racemic mixture of the cis enantiomers (−)-(2S,4R) and (+)-(2R,4S). Ketoconazole is a particularly preferred cortisol synthesis inhibitor for use in the treatment of diseases characterised by or associated with hypercortisolemia such as metabolic syndrome and diabetes mellitus type II. However this compound-is difficult to formulate and administer, in particular due to its low solubility. It is therefore surprising that effective controlled release compositions including ketoconazole as active ingredient can be prepared.

Reference to "ketoconazole" herein includes all four stereoisomers of the racemic cis/cis mixture known in the art as ketoconazole (Rotstein et al., J. Med. Chem. (1992) 35, 2818-2825) and derivatives of ketoconazole (and racemic and other mixtures of said stereoisomers). The Cis-2S, 4R and Cis-2R, 4S isomers are particularly preferred for use in accordance with the present invention. Rotstein teaches a method for preparation of the individual isomers which may be more conveniently prepared by resolution of the available racemic mixture by crystallisation.

Derivatives include structurally related compounds which have a similar ability to reduce cortisol activity in the body. Such derivatives having at least 30%, preferably at least 50% or at least 75 or 85% or more of the anti-cortisol activity of ketoconazole itself. Chemical modifications to ketoconazole which may be made without significantly reducing the activity of the compound will be obvious to the skilled man and/or may be prepared and tested by routine experimentation or modelling. At least the group of compounds represent by formula I below can be considered as derivatives of ketoconazole.

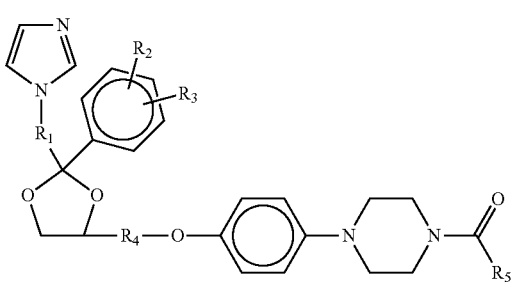

(I)

wherein R1 and R5 which may be the same or different represent a C1-3 alkyl group, R2 and R3 which may be the same or different represent hydrogen, a halogen atom or a methyl group substituted by one or more halogen atoms and R4 represents the group (CH2)nCH3 wherein n may be 0, 1 or 2. Ketoconazole itself is a compound of formula (I) wherein R1 and R5 are CH2, R2 and R3 are Cl and R4 is CH3. Further derivatives include salts of ketoconazole itself and of the derivatives discussed above. The formulations preferably contain one or other of the cis isomers of ketoconazole or a racemic or other mixture thereof The ketoconazole used in the preparation of the formulations of the invention is preferably in the form of particles of crystalline ketoconazole. The particles may be of different sizes, with diameters typically ranging from about 1 to about 500 μm more preferably from about 5 to about 200 These values are determined as the diameter at which 90% of the particles in the sample are no greater than. The particles will preferably be able to form a smooth paste with the release rate controlling substrate(s) and have suitable behavior for filling gelatine capsules.

Other antifungals include, but are not limited to: Miconazole, Oxiconazole, Clotrimazole, Econazole, Ketoconazole, Terbinafine, Naltifine, Ciclopirax, Tolnaftate, Amphotericin B, Miconazole, sertaconazole, sulconazole, cholorxylenol, clioquinol, butenafine, naftifine, nystatin, and clotrimazole and the like. An "antimycotic amount" of a given antifungal component means an amount at which the antifungal composition component hinders the growth of fungus associated with infections. The antifungal components may be present in the formulations of the present disclosure in an antimycotic amount that may range from about 0.01% to 10% by total weight of the treatment composition in a particular embodiment, and from 0.25% to 2% by total weight in a more particular embodiment.

The inventive compositions contain, as a preferred ingredient, a retinoic acid, which is selected from retinyl esters, retinol, retinal and retinoic acid, preferably retinol or retinyl ester. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are C1-C30esters of retinol, preferably C2-C20 esters, and most preferably C2, C3, and C16 esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, and retinyl oleate.

The preferred ester for use in the present invention is selected from retinyl palmitate, retinyl acetate and retinyl propionate, because these are the most commercially available and therefore the cheapest. Retinyl linoleate and retinyl oleate are also preferred due to their efficacy.

Retinol or retinyl ester is employed in the inventive composition in an amount of from about 0.001% to about 10% by weight, preferably in an amount of from about 0.01% to about 1% by weight, most preferably in an amount of from about 0.01% to about 0.5% by weight.

According to one embodiment, several skin disorders of proliferation and differentiation benefit from the treatment of the present invention. Such disorders even if not directly affected through the cholesterol synthesis pathway, could be indirectly affected and would benefit from the treatment.

A method of treating ichthyosis/ichthyosiform disorders comprising the administrations of Formulations 1 and 2.

A method of treating dry skin, atopic dermatitis, seborrheic dermatitis and other forms of dermatitis comprising the administrations of Formulations 1 and 2.

A method of treating psoriasis, vitiligo and other autoimmune/immune mediated skin diseases comprising the administrations of Formulations 1 and 2.

Using formulation 1, in two patients with CHILD (congenital hemidysplasia with ichthyosiform disorder) syndrome (FIGS. 3A-3B and 4A-4D) were treated. Similarly, in individuals with inherited forms of autosomal recessive ichthyosis (FIGS. 5A-5D and 6A-6B) were treated.

The combined cholesterol and statin will block the cholesterol synthesis pathway that has several toxic metabolites and at the same time will replace the cholesterol for the normal skin differentiation. The glycolic acid creams will help in desquamating the external keratotic part of the skin that allows the internal penetration of the cholesterol/statin combination.

Future application in dry skin, eczema, different forms of dermatitis, and psoriasis.

The term "effective amount" should be understood as meaning an amount of an active ingredient needed to achieve a desired therapeutic or cosmetic effect. For example, in a pharmaceutical composition of the invention an effective amount of an inhibitor of cholesterol synthesis is an amount which is sufficient, in the administration regimen of the pharmaceutical composition in the framework of treatment, to achieve an improvement in the skin's condition. In a cosmetic composition, an effective amount is an amount which causes an improvement in skin appearance.

"Co-administration" and "co-therapy" refer to the administration of two (or more) drugs in the same course of therapy in order to achieve a type or level of benefit not resulting from administration of either drug individually.

"Administration" means administering a drug or combination of drugs for at least one day, more often for at least seven days, even more often for at least fourteen days, even more often for at least one month, often for at least 4 months (120 days), and sometimes for several years. "Administering" or "administration of" a drug to a subject (and grammatical equivalents of this phrase) may refer to direct administration, including self-administration, and indirect administration, including the act of prescribing a drug. For example, a physician who instructs a patient to self-administer a drug and/or provides a patient with a prescription for a drug may be administering the drug to the patient.

The compounds of the present invention can be included in a composition, e.g., a pharmaceutical composition. The composition can be produced by combining one or more compounds of the present invention with an appropriate pharmaceutically-acceptable carrier, and can be formulated into a suitable preparation. Suitable preparations include, for example, preparations in solid, semi-solid, liquid, or gaseous forms such as tablets, capsules, powders, granules, ointments, solutions, injections, suppositories, inhalants, and aerosols, and other formulations known in the art for their respective routes of administration. In pharmaceutical dosage forms, a compound of the present invention can be used alone or in appropriate association, as well as in combination, with other pharmaceutically active compounds, including other effective amount compounds, as described herein.

Any suitable carrier can be utilized. Suitable carriers include pharmaceutically or physiologically acceptable carriers. The following methods and carriers are merely exemplary and are in no way limiting. In the case of oral preparations, a compound of the present invention can be administered alone or in combination with a therapeutically effective amount of at least one other compound. Compositions used in accordance with the present invention can further include at least one additional compound other than a compound of the present invention, for example, an additional effective amount or even an anticancer agent. The active ingredient(s) can be combined, if desired, with appropriate additives to make tablets, powders, granules, capsules, or the like.

Suitable additives can include, for example, conventional additives such as lactose, mannitol, corn starch or potato starch. Suitable additives also can include binders, for example, crystalline cellulose, cellulose derivatives, acacia, corn starch, or gelatins; disintegrants, for example, corn starch, potato starch or sodium carboxymethylcellulose; with lubricants such as talc or magnesium stearate. If desired, other additives such as, for example, diluents, buffering agents, moistening agents, preservatives, and/or flavoring agents, and the like, can be included in the composition.

The compounds used in accordance with the present invention can be formulated into a preparation for injection by dissolution, suspension, or emulsification in an aqueous or nonaqueous solvent, such as vegetable oil, synthetic aliphatic acid glycerides, esters of higher aliphatic acids, or propylene glycol (if desired, with conventional additives such as solubilizers, isotonic agents, suspending agents, emulsifying agents, stabilizers, and preservatives). The compounds of the present invention also can be made into an aerosol formulation to be administered via inhalation. Such aerosol formulations can be placed into pressurized acceptable propellants such as dichlorodifluoromethane, propane, nitrogen, and the like.

The compounds of the present invention can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature, but are solid at room temperature.

Unit dosage forms for oral or rectal administration such as syrups, elixirs, and suspensions can be provided wherein each dosage unit, e.g., teaspoonful, tablespoonful, tablet, or suppository contains a predetermined amount of the composition containing the compound of the present invention. Similarly, unit dosage forms for injection or intravenous administration can comprise a composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of at least one compound or compounds of the present invention (alone or, if desired, in combination with another therapeutic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual host.

The pharmaceutical composition of the invention can be prepared in the form of a solution, lotion, gel, cream, ointment, solid stick, aerosol or powder, or in other forms suited to administration topically, orally or by injection. Most of the topical products are formulated as either creams or ointments. A cream is a topical preparation used for application on the skin. Creams are semi-solid emulsions, which are mixtures of oil and water in which APIs (Active Pharmaceutical Ingredients) are incorporated. They are divided into two types: oil-in-water (OAV) creams which compose of small droplets of oil dispersed in a continuous water phase, and water-in-oil (W/O) creams which compose of small droplets of water dispersed in a continuous oily phase. Oil-in-water creams are user-friendly and hence cosmetically acceptable as they are less greasy and more easily washed with water. An ointment is a viscous semisolid preparation containing APIs, which are used topically on a variety of body surfaces. The vehicle of an ointment is known as ointment base. It is essential that the active drug penetrates the skin for the optimum bio-dermal efficacy. The particle size of the active drug plays an important role here. It is necessary that the active drug is available in colloidal or molecular dispersed state for the product being highly efficacious form. Also this is to be achieved in the safe pH compatible environment of skin (4.0 to 6.0). To achieve all these, it is essential to choose proper vehicles or co-solvents for the dissolution or dispersion of the drug. The product of the. present invention is highly efficacious due to the pronounced antifungal/anti-inflammatory & wound healing activity of the active ingredients, which are available in ultra micro-size, colloidal form, which enhances skin penetration.

Pharmaceutically acceptable carriers, for example, base, stabilizer, emulsifier to increase the stability of the said composition, and to be formulated into gel, gel-cream, or topical liquid solution, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can be readily made by a skilled practitioner to address the nature or severity of the condition being treated. Adjustments in dose also can be made on the basis of other factors such as, for example, the individual patient's overall physical health, sex, age, prior medical history, and the like.

In one embodiment, the method of the present invention includes co-administering a therapeutically effective amount of at least one compound of the present invention in combination with a therapeutically effective amount of at least one additional compound other than a compound of the present invention. For example, a compound of the present invention can be co-administered with an additional effective amount (as described previously).

The compounds of the present invention can be administered by any suitable route including, for example, oral administration, intramuscular administration, subcutaneous, intravenous administration, or the like. For example, one or more effective amounts of the present invention (or a composition thereof) can be administered as a solution that is suitable for intravenous injection or infusion, a tablet, a capsule, or the like, or in any other suitable composition or formulation as described herein.

Skin diseases, may include, but are not limited to, burns, wounds, general operative wounds, pernio, decubitus, funiculitis, impetigo, intertrigo, radiation ulcer, acne vulgaris or infectious eczematous dermatitis develop erythema, swelling, bulla, erosion, or ulcer etc., being accompanied with bacterial infections.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Use of Topical Glycolic Acid Plus a Lovastatin-Cholesterol Combination Cream for the Treatment of Autosomal Recessive Congenital Ichthyoses The Department of Dermatology at the American University of Beirut Medical Center maintains a large database of genodermatosis cases among Lebanese and Middle Eastern families. From this database, 15 patients were recruited with topical treatment-resistant lamellar ichthyosis that had undergone no oral treatment for at least 3 months. All participants had consanguineous parents and were clinically and genetically diagnosed with ARCI. The study was approved by the institutional review board at the American University of Beirut, and all patients provided their written informed consent.

Treatment consisted of 3 different components: glycolic acid, statin, and cholesterol. Glycolic acid, 10%, was applied on the face; glycolic acid, 15% or 20%, was applied on the body. The frequency of application varied from nightly application to every other night, depending on tolerability. The combination cream of lovastatin, 2%, and cholesterol, 2%, was applied every morning on all affected areas. All patients were asked if they would be willing to participate in a smaller left sided vs right sided trial, and those who agreed were asked to apply the combination lovastatin-cholesterol cream on 1 side of the body only (e.g., right arm and right leg) to assess the additive effects of the combination cream.

Patients were scheduled for monthly visits, for up to 3 months, during which they were provided with the study creams, and the ARCI was assessed for improvement. The primary outcome was clinical improvement after 3 months of treatment.

Scoring System

Each patient was given a severity score based on 5 criteria: (1) skin thickness and/or scaling; (2) pain, pruritus, and/or discomfort; (3) erythema; (4) impact of the condition on the ability to perform daily functions; and (5) the patient's subjective severity scoring, i.e., the patient's own assessment of the severity of the condition. The degree of improvement at follow-up was assessed by the percentage reduction in the severity score compared with baseline. A reduction of 0% to 9.9% was considered a poor response; 10.0% to 24.9%, a fair response; 25.0% to 49.9%, good response; 50% to 74.9%, very good response; and 75% to 100%, excellent response. Scoring Criteris are listed in Table 1.

TABLE 1

| Criterion | Maximum Score |
|---|---|
| Skin thickness/scaling | 20 |
| Pain/Pruritis/Discomfort | 20 |

TABLE 1-continued

| Criterion | Maximum Score |
|---|---|
| Erythema | 20 |
| Impact of the condition on the ability to perform daily functions | 20 |
| Patient severity scoring | 20 |
| Total score | 100 |

Results

A total of 15 patients with ARCI were enrolled in the study. The average patient age was 11.2 years (range, 2-38 years); 10 (67%) were male, and 5 (33%) were female. More information about the study participants and outcomes is available in the Supplement.

Primary Outcome

Figure 1B:
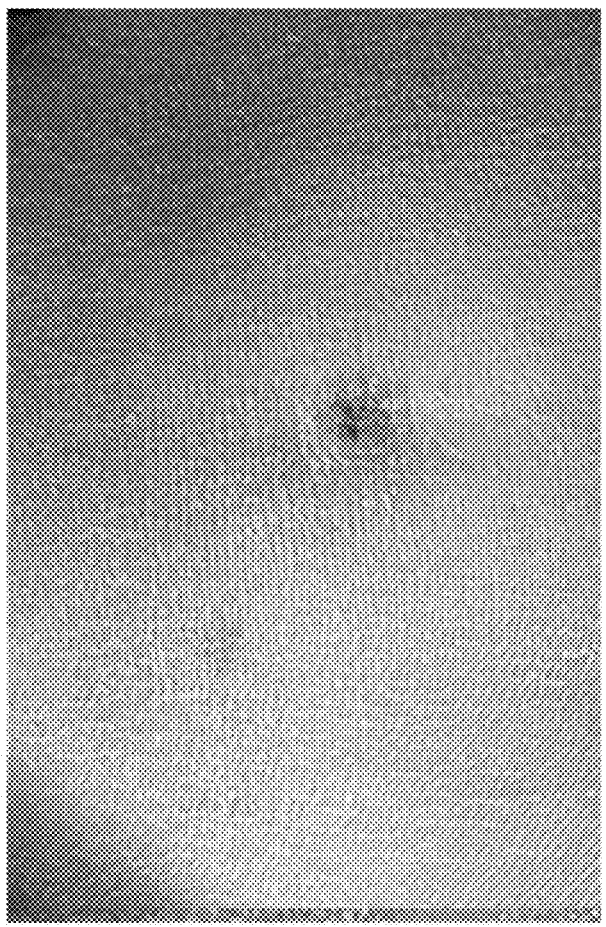
Figure 2A:
FIGS. 2A-2B are photographs of Patient 11 before (FIG. 2A) and 3 months after (FIG. 2B) treatment with the study medication. An excellent response was noted, i.e., 79.3% improvement from baseline in the disease severity score.
Figure 2B:
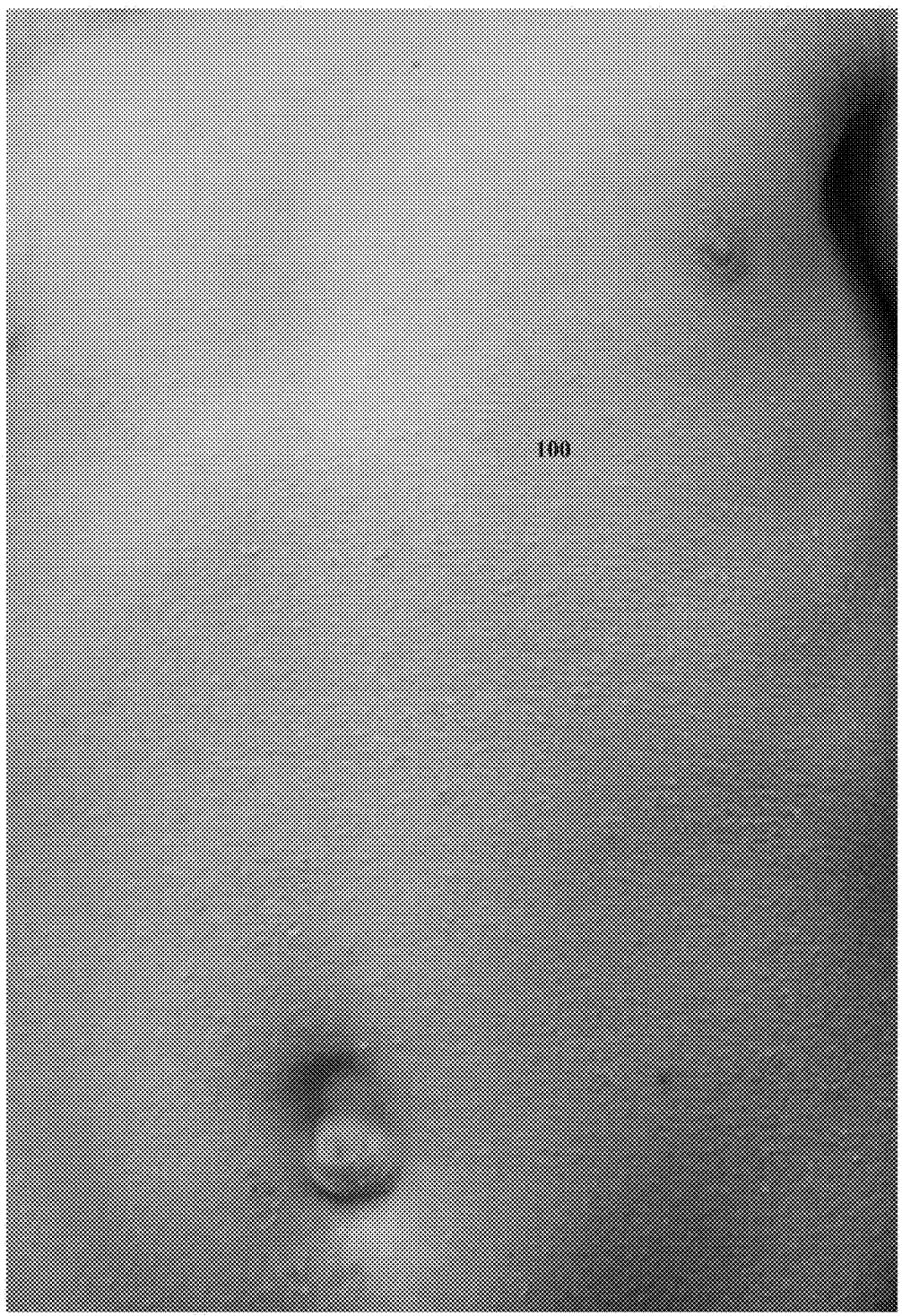

The average severity scores at baseline and 2- and 3-month follow-up evaluations were 60.8, 40.2, and 21.9, respectively. The average percentage reductions in the severity scores were 33.7% at 2 months (mild response) and 57.5% at 3 months (good response). Overall, at 2 months, 7 patients had achieved a mild response; 2 patients, a good response; and 6 patients, a very good response. At 3 months, 2 patients had achieved a mild response; 2 patients, a good response; 9 patients, a very good response (FIG. 1); and 2 patients, an excellent response (FIG. 2). Table 2 displays the results

TABLE 2

Response in patients who applied the combination of statin with cholesterol on the right side of the body only

| | 1 | | 2 | | 3 | | 4 | | 6 | |
|---|---|---|---|---|---|---|---|---|---|---|
| At Baseline | Left | Right | Left | Right | Left | Right | Left | Right | Left | Right |
| Skin thickness/scaling | 15 | 15 | 12 | 12 | 7 | 7 | 13 | 13 | 17 | 17 |
| Pain/pruritis/discharge | 7 | 7 | 7 | 7 | 4 | 4 | 8 | 8 | 10 | 10 |
| Erythema | 10 | 10 | 7 | 6 | 3 | 3 | 11 | 11 | 13 | 13 |
| Ability to perform daily functions | 5 | 5 | 7 | 7 | 3 | 3 | 7 | 7 | 10 | 10 |
| Patient severity scoring | 18 | 18 | 17 | 17 | 10 | 10 | 16 | 16 | 18 | 18 |
| Total score | 55 | 55 | 50 | 49 | 27 | 27 | 55 | 55 | 68 | 68 |
| At 2 months | | | | | | | | | | |
| Skin thickness/scaling | 15 | 15 | 10 | 8 | 7 | 7 | 8 | 7 | 15 | 16 |
| Pain/pruritis/discharge | 6 | 7 | 6 | 6 | 3 | 3 | 4 | 3 | 8 | 10 |
| Erythema | 9 | 7 | 6 | 6 | 3 | 2 | 9 | 8 | 13 | 13 |
| Ability to perform daily functions | 5 | 5 | 5 | 5 | 3 | 3 | 3 | 3 | 10 | 10 |
| Patient severity scoring | 17 | 17 | 17 | 17 | 10 | 10 | 8 | 6 | 17 | 17 |
| Total score | 52 | 51 | 44 | 42 | 26 | 25 | 32 | 27 | 63 | 66 |
| % change | −5.4545 | −7.27273 | −12 | −14.2857 | −3.7037 | −7.40741 | −41.818 | −50.909 | −7.35294 | −2.94118 |
| Response | Mild | Mild | Mild | Mild | Mild | Mild | Good | Very Good | Mild | Mild |
| At 3 months | | | | | | | | | | |
| Skin thickness/scaling | 9 | 7 | 6 | 5 | 4 | 2 | 6 | 5 | 14 | 16 |
| Pain/pruritis/discharge | 2 | 1 | 4 | 2 | 2 | 1 | 2 | 1 | 7 | 7 |
| Erythema | 4 | 3 | 4 | 3 | 2 | 2 | 4 | 3 | 13 | 12 |
| Ability to perform daily functions/to move | 2 | 2 | 2 | 2 | 1 | 1 | 2 | 2 | 10 | 10 |
| Patient severity scoring | 8 | 5 | 5 | 3 | 7 | 5 | 5 | 3 | 17 | 17 |
| Total score | 25 | 18 | 21 | 15 | 16 | 11 | 19 | 14 | 61 | 62 |
| % change | −54.545 | −67.2727 | −58 | −69.3878 | −40.7407 | −59.2593 | −65.455 | −74.545 | −10.2941 | −8.82353 |
| Response | Very good | Very good | Very good | Very good | Good | Very good | Very good | Very good | Mild | Mild |

Secondary Outcomes

Five patients applied the combination cream of lovastatin and cholesterol on the right side of the body only, while the glycolic acid was applied to both sides (patients 1, 2, 3, 4, and 6).

As detailed in Table 2, in all 5 of these patients, a better response was noted on the sides where the combination cream was applied compared with the sides where it was not. This points to a potentially significant role for the lovastatin-cholesterol combination in the treatment of ARCI. Adverse effects reported by patients were mild erythema, scaling, and burning. These effects were transient and resolved rapidly after altering the frequency of application.

Discussion

Cholesterol is an integral component of all cell membranes. It contributes to the barrier function of the epidermis. The "cholesterol sulfate cycle" is also essential for the development and maturation of keratinocytes. In the lower epidermis, cholesterol is sulfated by the enzyme cholesterol sulfotransferase (SULT2B1b) to form cholesterol sulfate, which is then desulfated by the enzyme steroid sulfatase in the outer epidermis.[3]

Studies suggest that cholesterol sulfate is not only a marker of differentiation but also a signaling molecule involved in the regulation of keratinocyte differentiation.[10,11] While many of the ichthyoses are associated with inherited disorders of lipid metabolism, the particular importance of the cholesterol cycle is highlighted in patients with x-linked ichthyosis due to loss of-function mutations in the steroid sulfatase gene. In the past, studies evaluating the therapeutic role of cholesterol in x-linked ichthyosis have failed to recognize the role of generated toxic metabolites in the pathogenesis of the disease. This explains, in part, the inconsistent results obtained after treatment with topical cholestero[4,5] Adding a topical statin to the treatment regimen allows the inhibition of endogenous cholesterol production, thus preventing the accumulation of toxic metabolites that may disrupt skin differentiation. Although the direct role of the cholesterol metabolic pathway is most clear in x-linked ichthyosis, this pathway also plays an important role in ARCI. Many of the genes that are mutated in ARCI are involved in lipid metabolism (SULT2B1, ALOX12B, ALOXE3, PNPLA1, CERS3, LIPN) and are either directly or indirectly linked to the cholesterol pathway.

The therapeutic efficacy of a treatment regimen was evaluated consisting of a glycolic acid, 10% to 20%, cream and a combination cream of lovastatin, 2%, with cholesterol, 2%, in the treatment of 15 patients with ARCI who had responded poorly to other topical medications. Glycolic acid was used as a keratolytic agent to allow for better penetration of the lovastatin-cholesterol combination cream. Interestingly, the average percentage reductions in the disease severity scores were 33.7% at 2 months (mild response) and 57.5% at 3 months (good response). Nine patients had very good responses, and 2 had excellent responses; ie, at least 75% of the patients had more than 50% improvement. Among the 5 patients who applied the lovastatin-cholesterol combination cream only on the right side of the body, significant improvement was improved when compared to the left side. Adverse effects were mild and transient and were limited to irritation and burning secondary to the glycolic acid.

In conclusion, our study points to potential benefits of a treatment regimen consisting of glycolic acid, 10% to 20%, cream and a combination cream of lovastatin, 2%, with cholesterol, 2%, in the treatment of patients with ARCI.

Example 2

CHILD Syndrome: A Modified Pathogenesis-Targeted Therapeutic Approach

Two female patients who were previously diagnosed with CHILD syndrome based on both clinical and genetic work-up. A cream based preparation with 2% cholesterol and 2% lovastatin; as well as a separate 12% glycolic acid cream was formulated. The determination of the glycolic acid percentage was based on the experience of our center as a tertiary center for genodermatoses including ichthyosis. The minimal glycolic acid percentage was chosen to be effective and with least side effects and accordingly increased the dose. Consequently, the 12% level was the appropriate concentration.

Case One

An 11-year-old girl presented to our institution with a 1 year history of growing asymptomatic slowly enlarging lesion in the right axilla. Additionally she had multiple asymptomatic skin lesions on the face, the trunk and extremities, on both sides, but more pronounced over the right side.

Figure 3A:
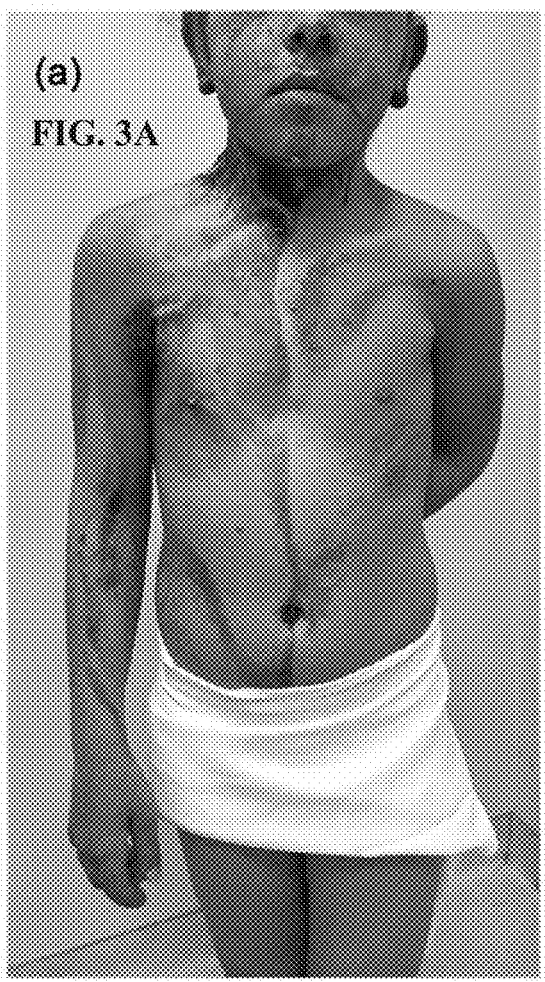
FIGS. 3A-3E are photographs of Case 1: Clinical features of patient with CHILD syndrome in case one.
Figure 3B:
Figure 3C:
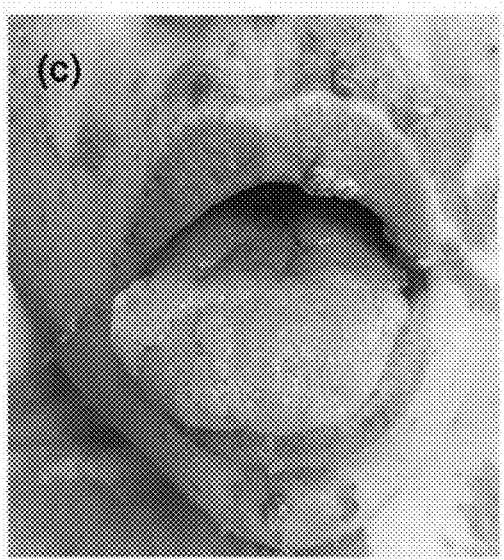
Figure 3D:
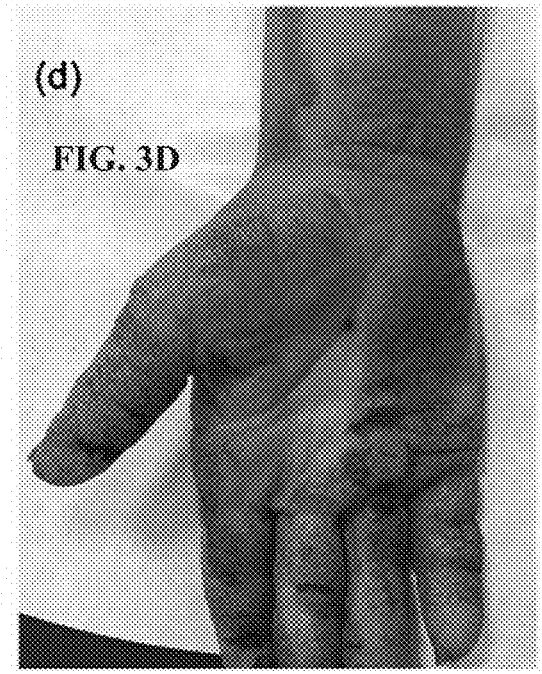
Figure 3E:
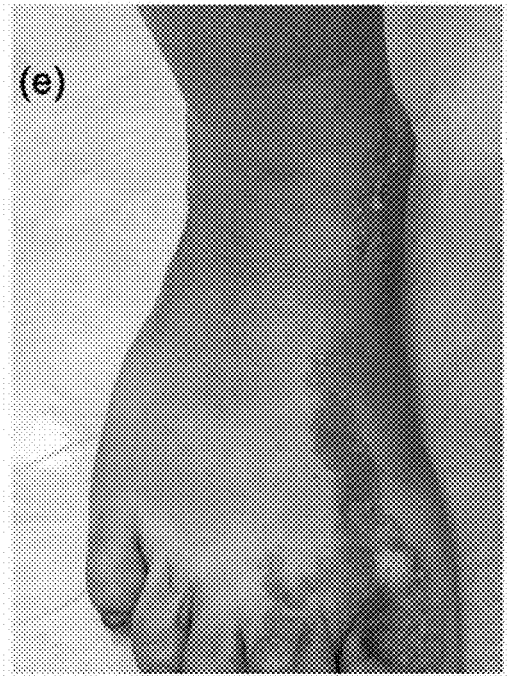
Figures 4A, 4B:
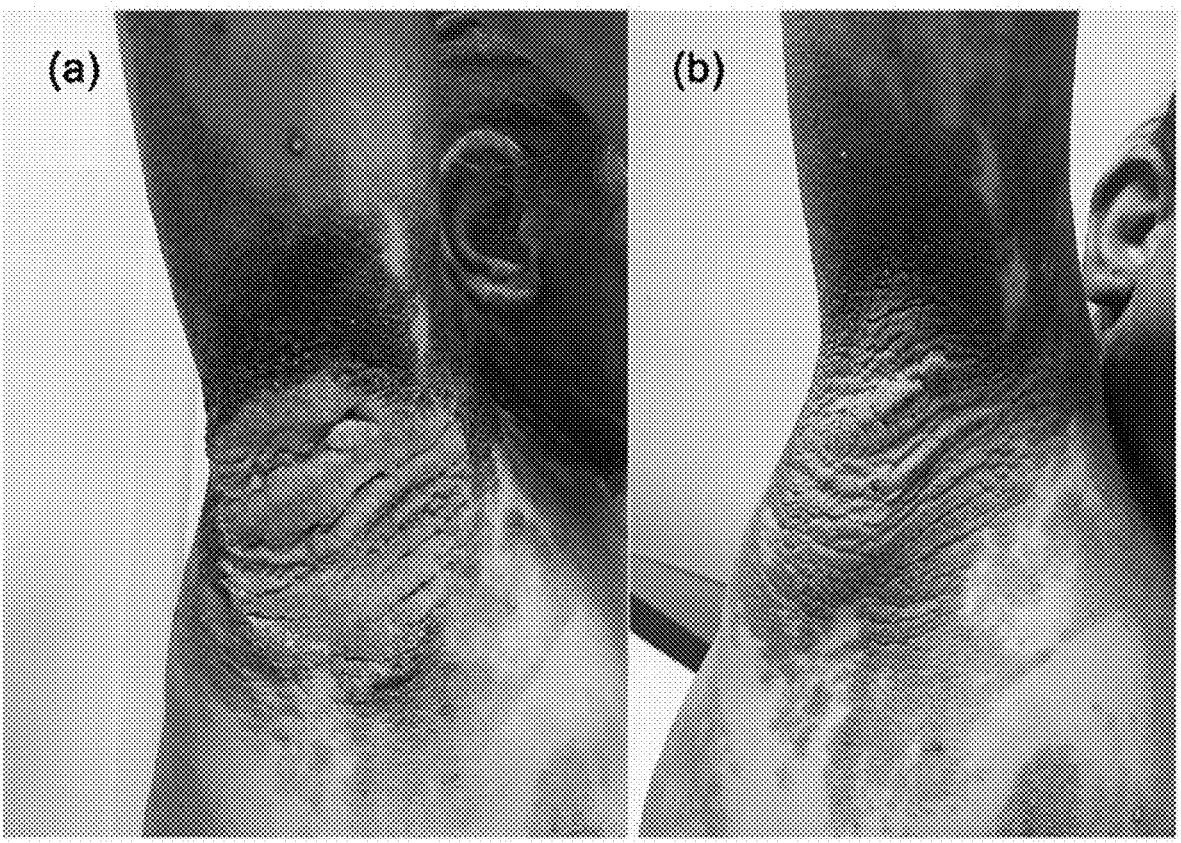
FIGS. 4A-4B are photographs of Case 1: The effect of 2% cholesterol and 2% lovastatin cream on verruciform xanthoma.
Figure 5A:
FIGS. 5A-5F are photographs of Case 2: The effect of 2% cholesterol and 2% lovastatin cream on verruciform xanthoma of the right foot.
Figure 5B:
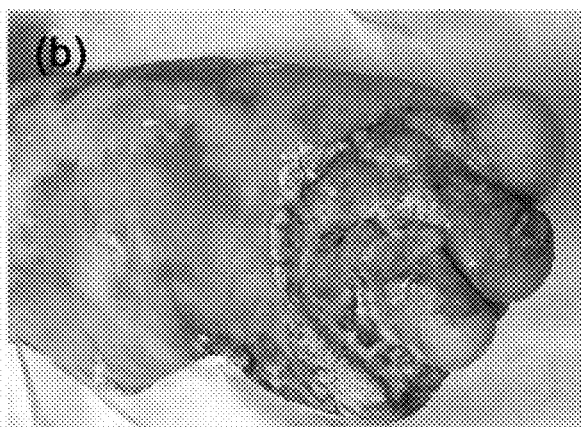
Figure 5C:
Figure 5D:
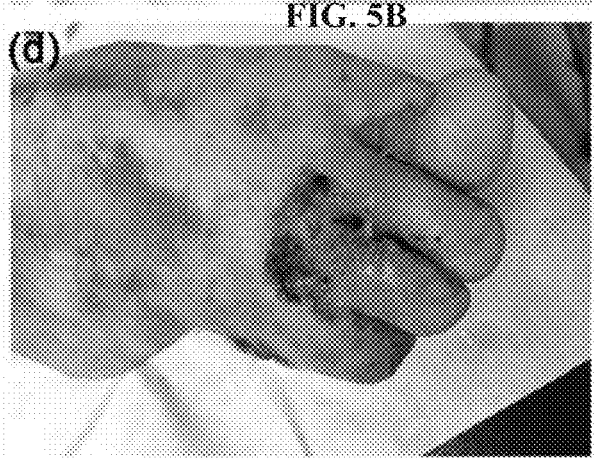
Figure 5E:
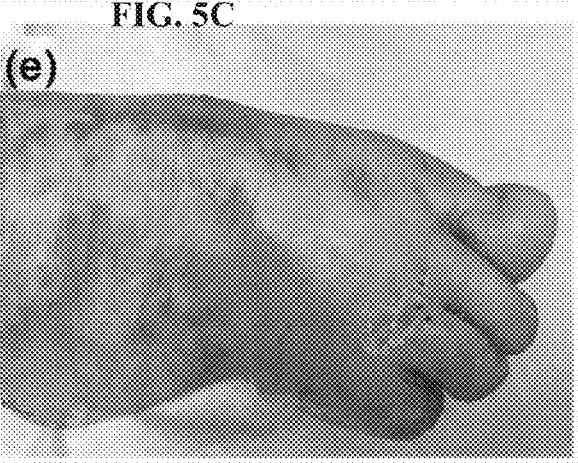
Figure 5F:
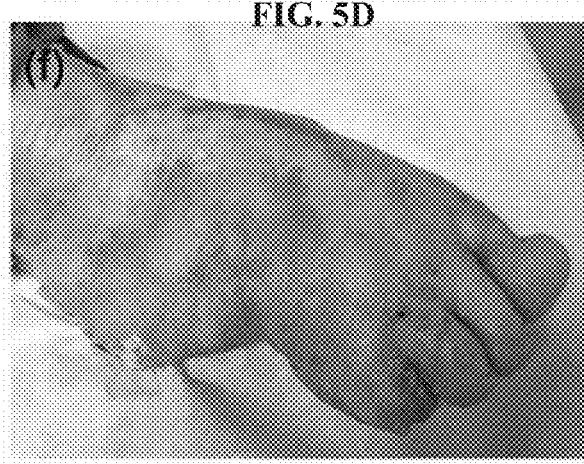

On examination, she had over the right axilla a large erythematous fleshy verrucous hyperkeratotic plaque (FIG. 3a). Diffusely, over her face, her trunk, and extremities, bilaterally, but more pronounced on the right side, she had brown linear plaques consisting of discrete and confluent verrucous papules, arranged along the lines of Blashko. These lesions appeared shortly after birth as erythematous plaques that progressively turned brown. Interestingly, the clinically recognizable inflammatory component was only present over the axillary region. Over her palms, bilaterally, she had linear hyperkeratotic thick yellowish plaques (FIG. 3d). She was born to a healthy multigravida mother after an uneventful pregnancy. Family history was negative for a similar condition.

Skin biopsy of the right axilla lesion showed a polypoid papillomatous lesion displaying foci of parakeratosis containing neutrophils and a mild superficial perivascular lymphoneutrophilic infiltrate with increased vascularity consistent with a verruciform xanthoma in the setting of CHILD syndrome. Clinical diagnosis of CHILD syndrome was confirmed by mutational analyses, which detected a missense mutation (p.A105V) in the coding region of the NAD(P) dependent steroid dehydrogenase-like protein (NSDHL) gene. Complete systemic workup was negative for any skeletal or internal organ abnormalities.

The right axilla verruciform xanthoma was treated with a cream containing 2% cholesterol and 2% lovastatin twice a day. As early as 4 weeks after initiation of therapy, the erythematous waxy lesion cleared leaving behind a healthy brown epidermal nevus continuous with the surrounding skin (FIG. 4). The patient was then lost to follow up. She then came back 8 months later with reappearance of the lesion, but to a much lesser extent. It cleared quickly 2 weeks after application of the cream twice a day, and she is been maintained since on two applications per week. Interestingly, the patient remained in remission for 6-7 months despite being off treatment.

Case Two

Our second patient was well known to us and she has already been the subject of a previous case report (Kurban et al., 2010). She is a 23-year old patient who presented to us 8 years ago with a verruciform xanthoma of the right lateral foot. She also had multiple asymptomatic skin lesions, predominantly over the right side, on the trunk and extremities, which appeared a few weeks after birth. Clinical diagnosis of CHILD syndrome was confirmed by mutational analyses, which detected the same missense mutation (p.A105V) in the coding region of the NAD(P) dependent steroid dehydrogenase-like protein (NSDHL) gene. Over the years, several treatments had been tried, including corticosteroids, vitamin D3 analogs and glycolic acid containing creams, to no avail. She had a surgical excision of the verruciform xanthoma in 2012, but it recurred quickly, with the appearance of the verruciform xanthoma at the site of injury. She also had a newverruciform xanthoma that developed on the lateral aspect of her left foot.

The patient was initially treated with the cream containing 2% cholesterol and 2% lovastatin twice daily, without any improvement of the thick lesions. This was followed by the addition of a cream containing 12% glycolic acid, which was applied once a day over both the right and left foot verruciform xanthomas (FIGS. 5a and 6a, respectively), as well as on the keratotic plaques over the dorsum of her right foot.

An appreciable response was seen after 8 weeks and lesions substantially decreased in size over a 12 months period leaving behind post-inflammatory hypopigmentation (FIGS. 5 and 6).

Discussion

The large range of skin lesions seen in CHILD syndrome is presumed to arise from accumulation of toxic metabolites along with the deficiency of the end product: cholesterol. Topical treatment with lovastatin inhibits HMG CoA reductase, the early rate-limiting enzyme in the cholesterol synthesis pathway and hence prevents the accumulation of toxic products, whereas topical treatment with cholesterol bypasses the defective cholesterol synthesis pathway and delivers the cholesterol required for normal stratum corneum function (Seeger & Paller, 2014).

To the best of our knowledge, only a handful number of patients were successfully treated using pathogenesis-based therapy since its introduction by Paller (Alexopoulos & Kakourou, 2015; Christiansen et al., 2015; Kiritsi et al., 2014; Paller et al., 2011; Seeger & Paller, 2014). Patients were treated twice daily with a 2% lovastatin/2% cholesterol cream to select lesions. Interestingly, the addition of 12% glycolic acid cream once a day, in our study, proved to be effective in helping the delivery of the combined cholesterol and statin cream through the thick keratotic scales resulting in higher efficiency and long term efficacy.

Clearing of abnormal lesions started as early as 4 weeks after beginning of therapy; and continuous application of the cream over an 18 months period helped decrease the bulky lesions progressively. Interestingly, the patient presented in case 1 was lost to follow up as she mistakenly thought that her lesions will resolve completely after the 3 month period of therapy and she did not return except upon the recurrence of her lesions which was nearly 8 months later. Thus, some patients might have long term remission despite stopping the treatment and additional data from other patients will help us and others formulate a better standard treatment program.

Until recently, surgical excision or dermabrasion has been preferred for CHILD nevus including its features of verruciform xanthoma, with subsequent skin grafting from an unaffected area (Fink-Puches, Soyer, Pierer, Kerl, & Happle, 2000; Konig et al., 2010). Our patient had a surgical excision with grafting from an uninvolved skin graft, and shortly after developed a new verruciform xanthoma. In a previous report, both axillae were replaced with uninvolved skin grafts but shortly developed CHILD nevus again at the surgical sites (Fink-Puches et al., 2000).

Hence, although the surgical excision of CHILD syndrome lesions has been for the most successful, the combination cream is proving itself to be an as effective but less costly approach.

In conclusion, both cholesterol and lovastatin have known safety profiles and are relatively inexpensive; they have shown an excellent response of CHILD syndrome lesions. Our study, confirms the efficacy of the pathogenesis targeted therapy. Furthermore, introducing some alterations to the preparation, such as adding glycolic acid in our case, might improve the treatment. Preparing the formula using nanoparticles could help decreasing the frequency of application and thus helping in achieving better compliance.

Example: Use of Two Combination Creams for the Treatment of Ichthyoses and Ichthyosiform Disorders In the present example, 24 treatment-resistant cases of Ichthyoses and Ichthyosiform disorders were tested. The lovastatin-cholesterol combination cream was used in addition to another cream consisting of a combination of glycolic acid, about 10%-tretinoin, and about 0.025%-ketoconazole, 2%.

Methods

The department of Dermatology at the American University of Beirut Medical Center is a referral center for genodermatoses all over Lebanon and the Middle East region. 25 patients with treatment-resistant Ichthyosis and Ichthyosiform disorders were enrolled, 17 of who were products of consanguineous marriage. Pregnant females were excluded. One patient was on oral isotretinoin and developed severe irritation within one week of our topical treatment and was therefore excluded from the study. The study was approved by the institutional review board at the American University of Beirut, and all patients provided their written informed consent.

Treatment creams were applied on specific areas chosen by both the patient and the physician. The combination cream of lovastatin at about 2% and cholesterol at about 2% was applied every morning. A glycerol-based moisturizer was applied every afternoon. The combination cream of glycolic acid at about 10%, tretinoin at about 0.025%, ketoconazole at about 2% was applied nightly or every other night depending on tolerability.

Patients were scheduled for monthly visits, during which they were provided with the study creams, scoring was done, and pictures were taken. The primary outcome was clinical improvement after about 2 and about 3 months of treatment. Some patients continued treatment beyond about 3 months. Unfortunately, because of the Lebanese revolution which started in October 2019 and the COVID-19 pandemic of 2020, some patients were not able to come to the clinic every month.

Scoring System

The same severity scoring system used as indicated above and in the previous study.[13] Five different criteria were assessed during each visit: (1) skin thickness and/or scaling; (2) pain, pruritus, and/or discomfort; (3) erythema; (4) impact of the condition on the ability to perform daily functions; and (5) the patient's subjective severity scoring, i.e., the patient's own assessment of the severity of his/her condition.

The degree of improvement at follow-up was assessed by the percentage reduction in the total severity score compared to baseline. A reduction of about 0% to about 9.9% was considered a poor response; about 10.0% to about 24.9%, a fair response; about 25.0% to about 49.9%, good response; about 50% to about 74.9%, very good response; and about 75% to about 100%, excellent response.

Results 24 patients completed at least 1 month of treatment. Half were males. The average patient age was 8.8 years (range, 1 month-26 years). The characteristics of the study participants are summarized in Table 1 shown in FIG. 8.

Primary Outcomes

The average severity score at baseline was 51.5. At 1, 2 and 3 months of follow-up, 20, 18 and 10 patients came to the clinic, respectively. The average severity scores were 31.2 at 1 month, 28.3 at 2 months, and 20.6 at 3 months. The average percentage reductions in the severity scores were 46% at 1 month (good response), 48.6% at 2 months (good response) and 63.8% at 3 months (very good response).

Overall, at 1 month, 3 patients had an excellent response; 7 patients a very good response; 5 patients a good response; 4 patients a fair response; and 1 patient a poor response. At 2 months, 4 patients had an excellent response; 5 patients a very good response; 6 patients a good response; 2 patients a fair response; and 1 patient a poor response. At 3 months, 3 patients had an excellent response; 6 patients a very good response; 1 patient a good response; and no patient had a poor or fair response, as shown in FIGS. 9-12 and FIGS. 13-19.

The scores of the patients are detailed in Table 1, as shown in FIG. 8.

Secondary Outcomes

At 4 and 5 months, 8 and 5 patients came for follow-up, respectively. The average severity scores were 20.6 at both 4 and 5 months. The average percentage reductions in the severity scores were 56.7% at 4 months, and 40.9 at 5 months. At 6 months, only one patient visited the clinic. He had an average severity score of 25 with a 50.9% percentage reduction from baseline (very good response).

Adverse effects reported by patients were mild and consisted mainly of erythema, scaling, and burning. These effects were managed by altering the frequency of application. One patient was on oral isotretinoin and developed severe irritation within 1 week of starting the creams. His symptoms did not resolve with fewer weekly applications of the creams. He withdrew from the study and was excluded from the analysis.

Discussion

Cholesterol is important for the formation of the physiologic skin barrier. In fact, many of the genes mutated in the Ichthyoses are related to cholesterol metabolism, either directly or indirectly.[13,14] Topical cholesterol, either alone or in combination with lovastatin, has been previously used for the treatment of few skin diseases, including X-linked ichthyosis[15,16], CHILD syndrome (congenital hemidysplasia ichthyosis and limb defects)[17-20], and ARCI[13]. Adding the statin increases treatment efficacy by inhibiting the formation of toxic metabolites in the endogenous cholesterol synthetic pathway.

Glycolic acid and tretinoin are keratolytics which help in shedding the excess skin and allow for a better penetration of the other cream. Furthermore, retinoids are important for the regulation of cell growth, differentiation and apoptosis.[21] As for ketoconazole, studies have shown that it has anti-inflammatory properties[22] and it inhibits cholesterol production[23,24] and the degradation of retinoids.[25]

The therapeutic efficacy of two combination creams in the treatment of ichthyosis and ichthyosiform disorders. The first cream consisted of lovastatin at about 2%, with cholesterol at about 2% and the second cream of glycolic acid at about 10%, tretinoin at about 0.025%-ketoconazole at about 2%. The average percentage reductions in the severity scores were 46% at 1 month (good response), 48.6% at 2 months (good response) and 63.8% at 3 months (very good response). Adverse effects were mild and manageable and consisted of irritation secondary to the night cream.

Conclusion

In conclusion, our study indicates the potential benefit of a treatment regimen consisting of a combination of about 2% cholesterol with about 2% lovastatin, with another combination of about 10% glycolic acid with about 0.025% tretinoin, and about 2% ketoconazole, in Ichthyoses and Ichthyosiform disorders.

References

1. Oji V, Tadini G, Akiyama M, et al. Revised nomenclature and classification of inherited ichthyoses: results of the First Ichthyosis Consensus Conference in Sorèze 2009. J Am Acad Dermatol. 2010;63(4):607-641. doi:10.1016/j aad.2009.11.020

2. Hernández-Martin A, Aranegui B, Martin-Santiago A, Garcia-Doval I. A systematic review of clinical trials of treatments for the congenital ichthyoses, excluding ichthyosis vulgaris. J AmAcad Dermatol. 2013;69(4): 544-549.e8. doi:10.1016/j.jaad.2013.05.017

3. Elias PM, Williams ML, Choi EH, Feingold KR. Role of cholesterol sulfate in epidermal structure and function: lessons from X-linked ichthyosis. Biochim Biophys Acta. 2014;1841(3):353-361. doi:10.1016/j.bbalip.2013.11.009

4. Lykkesfeldt G, Hoyer H. Topical cholesterol treatment of recessive X-linked ichthyosis. Lancet. 1983;2(8363): 1337-1338. doi:10.1016/S0140-6736 (83)91093-0.

5. Ibsen HH, Brandrup F, Secher B. Topical cholesterol treatment of recessive X-linked
ichthyosis. Lancet. 1984;2(8403):645. doi:10.1016/ S0140-6736(84)90642-1

6. Alexopoulos A, Kakourou T. CHILD syndrome: successful treatment of skin lesions with topical simvastatin/ cholesterol ointment—a case report. Pediatr Dermatol. 2015;32(4):e145-e147. doi:10.1111/pde.12587

7. Kiritsi D, Schauer F, Wolfle U, et al. Targeting epidermal lipids for treatment of Mendelian disorders of cornification. Orphanet J Rare Dis. 2014;9:33. doi:10.1186/1750-1172-9-33

8. Christiansen A G, Koppelhus U, Sommerlund M. Skin abnormalities in CHILD syndrome successfully treated with pathogenesis-based therapy. Acta Derm Venereol. 2015;95 (6):752-753. doi:10.2340/00015555-2044

9. Bergqvist C, Abdallah B, Hasbani DJ, et al. CHILD syndrome: a modified pathogenesis-targeted therapeutic approach. Am J Med Genet A. 2018;176 (3):733-738. doi: 10.1002/ajmg.a.38619

10. Shimada M, Matsuda T, Sato A, et al. Expression of a skin cholesterol sulfotransferase, St2b2, is a trigger of epidermal cell differentiation. Xenobiotica. 2008;38(12): 1487-1499. doi:10.1080/00498250802488593

11. Hanyu O, Nakae H, Miida T, et al. Cholesterol sulfate induces expression of the skin barrier protein filaggrin in normal human epidermal keratinocytes through induction of RORa. Biochem Biophys Res Commun. 2012;428(1):99-104. doi:10.1016/j.bbrc.2012.10.013.

12. Hernandez-Martin A, Aranegui B, Martin-Santiago A, Garcia-Doval I. A systematic review of clinical trials of treatments for the congenital ichthyoses, excluding ichthyosis vulgaris. J Am Acad Dermatol. 2013;69(4):544-549 e548.

13. Khalil S, Bardawil, T., Saade, S., Chedraoui, A., Ramadan, N., Hasbani, D. J., Abbas, O., Nemer, G., Rubeiz, N. and Kurban, M. Use of Topical Glycolic Acid Plus a Lovastatin-Cholesterol Combination Cream for the Treatment of Autosomal Recessive Congenital Ichthyoses. JAMA dermatology. 2018;154(11):1320-1323.

14. Elias P M, Williams M L, Choi E H, Feingold K R. Role of cholesterol sulfate in epidermal structure and function: lessons from X-linked ichthyosis. Biochim Biophys Acta. 2014;1841(3):353-361.

15. Lykkesfeldt G, Hoyer H. Topical cholesterol treatment of recessive X-linked ichthyosis. Lancet. 1983;2(8363):1337-1338.

16. Ibsen H H, Brandrup F, Secher B. Topical cholesterol treatment of recessive X-linked ichthyosis. Lancet. 1984;2(8403):645.

17. Alexopoulos A, Kakourou T. CHILD Syndrome: Successful Treatment of Skin Lesions with Topical Simvastatin/Cholesterol Ointment—A Case Report. Pediatr Dermatol. 2015;32(4):e145-147.

18. Kiritsi D, Schauer F, Wolfle U, et al. Targeting epidermal lipids for treatment of Mendelian disorders of cornification. Orphanet J Rare Dis. 2014;9:33.

19. Christiansen A G, Koppelhus U, Sommerlund M. Skin Abnormalities in CHILD Syndrome Successfully Treated with Pathogenesis-based Therapy. Acta Derm Venereol. 2015;95(6):752-753.

20. Bergqvist C, Abdallah B, Hasbani D J, et al. CHILD syndrome: A modified pathogenesis-targeted therapeutic approach. Am J Med Genet A. 2018;176(3):733-738.

21. Khalil S, Bardawil T, Stephan C, et al. Retinoids: a journey from the molecular structures and mechanisms of action to clinical uses in dermatology and adverse effects. J Dermatolog Treat. 2017;28(8):684-696.

22. Van Cutsem J, Van Gerven F, Cauwenbergh G, Odds F, Janssen P A. The antiinflammatory effects of ketoconazole. A comparative study with hydrocortisone acetate in a model using living and killed Staphylococcus aureus on the skin of guinea-pigs. J Am Acad Dermatol. 1991;25(2 Pt 1):257-261.

23. Kraemer F B, Spilman S D. Effects of ketoconazole on cholesterol synthesis. J Pharmacol Exp Ther. 1986;238(3):905-911.

24. Strandberg T E, Tilvis R S, Miettinen T A. Effects of ketoconazole on cholesterol synthesis and precursor concentrations in the rat liver. Lipids. 1987;22(12):1020-1024.

25. Van Wauwe J P, Coene M C, Goossens J, Van Nijen G, Cools W, Lauwers W. Ketoconazole inhibits the in vitro and in vivo metabolism of all-trans-retinoic acid. J Pharmacol Exp Ther. 1988;245(2):718-722.

Alexopoulos, A., & Kakourou, T. (2015). CHILD syndrome: Successful treatment of skin lesions with topical simvastatin/cholesterol ointment-A case report. Pediatric Dermatology, 32(4), 145-147. https://doi.org/10.1111/pde.12587

Bornholdt, D., Konig, A., Happle, R., Leveleki, L., Bittar, M., Danarti, R., Grzeschik, K. H. (2005). Mutational spectrum of NSDHL in CHILD syndrome. Journal of Medical Genetics, 42(2), e17. https://doi.org/10.1136/jmg.2004.024448

Christiansen, A. G., Koppelhus, U., & Sommerlund, M. (2015). Skin abnormalities in CHILD syndrome successfully treated with pathogenesis-based therapy. Acta Dermato-Venereologica, 95(6), 752-753. https://doi.org/10.2340/00015555-2044

Fink-Puches, R., Soyer, H. P., Pierer, G., Kerl, H., & Happle, R. (1997). Systematized inflammatory epidermal nevus with symmetrical involvement: An unusual case of CHILD syndrome? Journal of the American Academy of Dermatology, 36(5), 823-826. https://doi.org/10.1016/S0190-9622(97)70031-8

Fink-Puches, R., Soyer, H. P., Pierer, G., Kerl, H., & Happle, R. (2000). Surgical treatment of CHILD nevus. European Journal of Dermatology, 10(4), 262-264.

Happle, R. (1990).Ptychotropism as a cutaneous feature of the CHILDsyndrome. Journal of the American Academy of Dermatology, 23(4 Pt 1), 763-766.

Happle, R., Koch, H., & Lenz, W. (1980). The CHILD syndrome. Congenital hemidysplasia with ichthyosiform erythroderma and limb defects. European Journal of Pediatrics, 134(1), 27-33.

Kiritsi, D., Schauer, F., Wolfle, U., Valari, M., Bruckner-Tuderman, L., Has, C., & Happle, R. (2014). Targeting epidermal lipids for treatment of Mendelian disorders of cornification. Orphanet Journal of Rare Diseases, 9, 33. https://doi.org/10.1186/1750-1172-9-33

Konig, A., Happle, R., Bornholdt, D., Engel, H., & Grzeschik, K. H. (2000). Mutations in the NSDHL gene, encoding a 3beta-hydroxysteroid dehydrogenase, cause CHILD syndrome. American Journal of Medical Genetics, 90(4), 339-346.

Konig, A., Happle, R., Fink-Puches, R., Soyer, H. P., Bornholdt, D., Engel, H., & Grzeschik, K.-H. (2002). A novel missense mutation of NSDHL in an unusual case of CHILD syndrome showing bilateral, almost symmetric involvement. Journal of the American Academy of Dermatology, 46(4), 594-596. https://doi.org/10.1067/mjd.2002.113680

Konig, A., Skrzypek, J., Löffler, H., Oeffner, F., Grzeschik, K. H., & Happle, R. (2010). Donor dominance cures CHILD nevus. Dermatology, 220(4), 340-345.

Kurban, M., Abbas, O., Ghosn, S., & Kibbi, A. G. (2010). Late evolution of giant verruciform xanthoma in the setting of CHILD syndrome. Pediatric Dermatology, 27(5), 551-553. https://doi.org/10.1111/j.1525-1470.2010.01276.x Paller, A. S., van Steensel, M. A., Rodriguez-Martin, M., Sorrell, J., Heath, C., Crumrine, D., . . . Elias, P. M. (2011). Pathogenesis-based therapy reverses cutaneous abnormalities in an inherited disorder of distal cholesterol metabolism. Journal of Investigative Dermatologyl, 131(11), 2242-2248. https://doi.org/10.1038/jid.2011.189

Seeger, M. A., & Paller, A. S. (2014). The role of abnormalities in the distal pathway of cholesterol synthesis in the Congenital Hemidysplasia with Ichthyosiform erythroderma and Limb Defects (CHILD) syndrome. Biochimica et Biophysica Acta, 1841(3), 345-352. https://doi.org/10.1016/j .bbalip.2013.09.006

Xu, X. L., Huang, L. M., Wang, Q., & Sun, J. F. (2015). Multiple verruciform xanthomas in the setting of congenital hemidysplasia with ichthyosiform erythroderma and limb defects syndrome. Pediatric Dermatology, 32(1), 135-137. https://doi.org/10.1111/pde.12198

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of treating a skin condition comprising: administering a first combination including cholesterol at about 2%, a statin at about 2% and glycolic acid between about 10% and about 20% once daily to a subject; applying a second combination consisting of about 10% glycolic acid, about 2% ketoconazole and about 0.025% retinoic acid once daily to the subject; applying the first and the second combination for 1 month; and achieving a reduction of severity score;
   wherein the subject has a treatment-resistant Ichthyosis and Ichthyosiform disorder with a baseline severity score ranging from 5 to 90,
   wherein the severity score is based on 5 criteria: (1) skin thickness and/or scaling; (2) pain, pruritus, and/or discomfort; (3) erythema; (4) impact of the condition on the ability to perform daily functions; and (5) the subject's severity scoring based upon the subject's own assessment of the severity of the condition.

2. The method of claim 1, wherein said statin is selected from the group consisting of: pitavastatin, atorvastatin, rosuvastatin, fluvastatin, lovastatin, pravastatin and simvastatin.

3. The method of claim 2, wherein said first combination is administered in the form of a cream base or said second combination is administered in a form selected from the group consisting of: a solution, lotion, gel, cream, ointment, solid stick, aerosol, powder, and other forms suited to administration topically.

4. The method of claim 1, wherein said first combination and second combination are a pharmaceutical composition with a pharmaceutically-acceptable carrier.

5. The method of claim 1, wherein said first combination and second combination are encapsulated with a delivery system designed to provide prolonged release in the skin.

6. The method of claim 3, wherein the ichthyosis is selected from the group consisting of Autosomal Recessive Congenital Ichthyosis (ARCI), and congenital hemidysplasia ichthyosis and limb defects (CHILD) syndrome.

7. The method of claim 1, wherein the subject is a member of a group of subjects with a baseline average severity score of 52.

8. The method of claim 7, wherein the severity score is reduced to an average of 31 for 20 subjects.

9. The method of claim 7, wherein the first combination and the second combination is applied for 2 months.

10. The method of claim 9, wherein the severity score is reduced to an average of 28 for 17 subjects.

11. The method of claim 7, wherein the first combination and the second combination is applied for three months.

12. The method of claim 11, wherein the severity score is reduce to an average of 21 for 10 subjects.

13. The method of claim 1, wherein said statin is lovastatin.

* * * * *